US008901170B2

(12) United States Patent
Pohlman et al.

(10) Patent No.: US 8,901,170 B2
(45) Date of Patent: Dec. 2, 2014

(54) MALONONITRILE COMPOUNDS

(75) Inventors: Matthias Pohlman, Freinsheim (DE); Michael Hofmann, Bad Dürkheim (DE); Henricus Maria Martinus Bastiaans, Usingen (DE); Michael Rack, Eppelheim (DE); Deborah L. Culbertson, Fuquay Varina, NC (US); Hassan Oloumi-Sadeghi, Raleigh, NC (US); Takeo Hokama, Mountain View, CA (US); Christopher Palmer, San Jose, CA (US)

(73) Assignee: BASF SE, Ludwigshafen (DE)

( * ) Notice: Subject to any disclaimer, the term of this patent is extended or adjusted under 35 U.S.C. 154(b) by 1387 days.

(21) Appl. No.: 12/305,658

(22) PCT Filed: Jun. 22, 2007

(86) PCT No.: PCT/EP2007/056249
§ 371 (c)(1),
(2), (4) Date: Dec. 19, 2008

(87) PCT Pub. No.: WO2007/147888
PCT Pub. Date: Dec. 27, 2007

(65) Prior Publication Data
US 2010/0215777 A1 Aug. 26, 2010

Related U.S. Application Data

(60) Provisional application No. 60/815,728, filed on Jun. 22, 2006.

(51) Int. Cl.
*A01N 37/34* (2006.01)
*A61K 31/275* (2006.01)
*A01N 33/00* (2006.01)
*A01N 43/00* (2006.01)
*A01N 59/02* (2006.01)
*A61K 33/04* (2006.01)
*A61K 31/00* (2006.01)
*A61P 33/00* (2006.01)
*C07C 323/60* (2006.01)
*C07C 255/13* (2006.01)
*A01N 47/02* (2006.01)
*C07C 255/10* (2006.01)
*C07C 317/44* (2006.01)

(52) U.S. Cl.
CPC .............. *C07C 255/10* (2013.01); *A01N 37/34* (2013.01); *C07C 2101/14* (2013.01); *C07C 323/60* (2013.01); *C07C 255/13* (2013.01); *A01N 47/02* (2013.01); *C07C 317/44* (2013.01)
USPC .............. 514/526; 424/705; 514/65; 514/75; 514/242; 514/277; 514/373; 514/403; 514/435; 514/476; 514/519; 514/520; 514/523; 514/524; 514/525; 514/639; 558/303

(58) Field of Classification Search
None
See application file for complete search history.

(56) References Cited

U.S. PATENT DOCUMENTS

2004/0138065 A1   7/2004   Otaka et al.

FOREIGN PATENT DOCUMENTS

| EP | 1 555 259 | 7/2005 |
|---|---|---|
| JP | 2002 284608 | 10/2002 |
| JP | 2004 99593 | 4/2004 |
| JP | 2004 99597 | 4/2004 |
| WO | WO 02/089579 | 11/2001 |
| WO | WO 02/090320 | 11/2002 |
| WO | WO 02/090321 | 11/2002 |
| WO | WO 2004/006677 | 1/2004 |
| WO | WO 2004/020399 | 3/2004 |
| WO | WO 2005/063694 | 7/2005 |
| WO | WO 2005/068423 | 7/2005 |
| WO | WO 2005/068432 | 7/2005 |

OTHER PUBLICATIONS

Morissette et al., High-throughput crystallization: polymorphs, salts, co-crystals and solvates of pharmaceutical solids, Advanced Drug Delivery Reviews (2004), vol. 56, pp. 275-300.*
International Search Report for International Application No. PCT/EP2007/056249; Date of Completion: Sep. 21, 2007; Date of Mailing: Oct. 10, 2007.
International Preliminary Report on Patentability for International Application No. PCT/EP2007/056249; Date of Submission: Apr. 22, 2008; Date of Completion: Sep. 19, 2008.
Brückner, R. et al., "Substitutions and dehydrogenations by 2,2-bis(trifluoromethyl)ethylene-1,1-dicarbonitrile via hydride abstraction", Tetrahedron Letters, 32(16), 1875-1878 (1991).
Brückner, R. et al., "The electron-deficient olefin 2,2-bis(trifluoromethyl)ethylene-1,1-dicarbonitrile: Hydride abstractions from allyl and isobutenyl ethers and thioethers", Journal of Organic Chemistry, 56(5), 1677-1679 (1991).
Haas, A. et al., "Michael additions to trifluoromethylvinyl sulfone", Journal of Fluorine Chemistry, 20, 99-105 (1982).
Huisgen, V.R. et al., "Zur Konformation der zwitterionischen zwischenstufen aus tetracyanäthylen and alkyl-propenyläthern", Angewandte Chemie, 86(1), 48-49 (1974).
Nakamura, H. et al., "Palladium-catalyzed alkoxyallylation of activated olefins", Journal of the American Chemical Society, 120, 6838-6839 (1998).
Swaringen, R. et al., "Reaction of orthoformates with acidic methines," Journal of Organic Chemistry, 44, 4825-4829 (1979).

* cited by examiner

*Primary Examiner* — Abigail Fisher
*Assistant Examiner* — Frank Choi
(74) *Attorney, Agent, or Firm* — Brinks Gilson & Lione

(57) ABSTRACT

Compounds of formula (I) wherein the symbols have the meaning given in the specification, as well as processes for preparing the compounds (I), pesticidal compositions and synergistic mixtures comprising compounds (I), methods for the control of insects, acarids or nematodes by contacting the pests or their food supply, habitat or breeding grounds with a pesticidally effective amount of compounds formula (I), and a method for treating, controlling, preventing or protecting animals against infestation or infection by parasites which comprises orally, topically or parenterally administering or applying to the animals a parasiticidally effective amount of compounds of formula (I).

14 Claims, No Drawings

MALONONITRILE COMPOUNDS

The invention relates to derivatives of malononitrile, a process for their production and their use for controlling pests.

In spite of the commercial insecticides, acaricides and nematicides available today, damage to crops, both growing and harvested, caused by insects and nematodes still occurs. Therefore, there is continuing need to develop new and more effective insecticidal, acaricidal and nematicidal agents.

Pesticidal compounds exhibiting a dicyanoalkane moiety have been described in a number of patent applications: JP 2002 284608, WO 02/089579, WO 02/090320, WO 02/090321, WO 04/006677, WO 04/020399, JP 2004 99593, JP 2004 99597, WO 05/068432, WO 05/064823, EP 1555259, and WO 05/063694.

However, as the demands on modem pesticides concerning e.g. efficacy, spectrum, safety, environmental behaviour, toxicology, and economic production are steadily increasing, there is a continuous task to develop new pesticides showing improvements in at least one of these aspects.

It has now been found that this task is achieved by malononitrile compounds of a certain substitution pattern.

Accordingly, in one aspect of the invention there are provided compounds of formula (I),

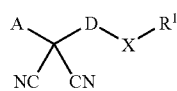

(I)

wherein
A is D-X—$R^1$ or Q;
X is, independently, oxygen or $S(=O)_n$;
n is 0, 1 or 2;
$R^1$ is, independently, $C_1$-$C_{10}$-alkyl, $C_1$-$C_{10}$-haloalkyl, $C_2$-$C_6$-alkenyl, $C_2$-$C_6$-haloalkenyl, $C_2$-$C_{10}$-alkynyl, $C_3$-$C_{10}$-haloalkynyl, $C_3$-$C_{10}$-cycloalkyl, $C_3$-$C_{10}$-halocycloalkyl, $C_3$-$C_{10}$-cycloalkenyl, $C_3$-$C_{10}$-halocycloalkenyl,
  phenyl or a 5- to 6-membered heteroaromatic ring system which contains 1 to 4 heteroatoms selected from oxygen, nitrogen and sulfur, which heteroaromatic ring is bonded to the X atom via a carbon atom of the ring, and which phenyl or which heteroaromatic ring may be bonded via a $C_1$-$C_{10}$-alkyl group thus forming an aryl-$C_1$-$C_{10}$-alkyl or hetaryl-$C_1$-$C_{10}$-alkyl moiety,
  wherein phenyl or the heteroaromatic ring may be fused to a ring selected from phenyl and a 5- to 6-membered saturated, partially unsaturated or aromatic heterocyclic ring which contains 1 to 3 heteroatoms selected from oxygen, nitrogen and sulfur,
  wherein the hydrogen atoms in the above groups $R^1$ may be partially or in total be replaced by any combination of groups $R^2$;
D is, independently, a saturated or partially unsaturated hydrocarbon chain with one to 5 carbon chain atoms or $C_3$-$C_6$-cycloalkyl, wherein the hydrogen atoms of this chain or of this cycloalkyl may all or in part be replaced with any combination of groups selected from $R^3$;
  $R^2$ is halogen, cyano, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, tri($C_1$-$C_{10}$)alkylsilyl, or
  phenyl or a 5- to 7-membered saturated or partially unsaturated heterocyclic ring which contains 1 to 3 heteroatoms selected from oxygen, sulfur and nitrogen or a 5- to 6-membered heteroaromatic ring system which contains 1 to 4 heteroatoms selected from oxygen, nitrogen and sulfur, which phenyl or which heterocyclic or heteroaromatic ring may be bonded via an oxygen or a sulfur atom, or
  two groups $R^2$ together with the carbon atom of the hydrocarbon chain may form a 3- to 7-membered saturated or partially unsaturated heterocyclic ring which contains 1 to 3 heteroatoms selected from oxygen, sulfur and nitrogen,
  wherein the above groups $R^2$ are unsubstituted, or the hydrogen atoms in these groups may all or in part be replaced with any combination of groups selected from $R^a$;
$R^3$ is halogen, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, $C_1$-$C_6$-alkoxycarbonyl, $C_1$-$C_6$-alkenyloxycarbonyl, $C_1$-$C_6$-alkylamino, di($C_1$-$C_6$-alkyl)amino, tri($C_1$-$C_{10}$)alkylsilyl, or
  phenyl or a 5- to 7-membered saturated or partially unsaturated heterocyclic ring which contains 1 to 3 heteroatoms selected from oxygen, sulfur and nitrogen or a 5- to 6-membered heteroaromatic ring system which contains 1 to 4 heteroatoms selected from oxygen, nitrogen and sulfur, which phenyl and which heterocyclic or heteroaromatic ring may be bonded via an oxygen or a sulfur atom,
  wherein the above groups $R^3$ are unsubstituted, or the hydrogen atoms in these groups may all or in part be replaced with any combination of groups selected from $R^a$, or
the moiety $R^3$-D-X—$R^1$ together may form a saturated or unsaturated ring of formula α

(α)

which may have 5 to 7 ring members and besides X 1 to 2 further heteroatoms selected from oxygen, sulfur and nitrogen and which ring may be substituted with 1 to 5 groups selected from $R^a$, or
the moiety $R^3$-D-X—$R^1$ together may form a group of formula β wherein x is 1 to

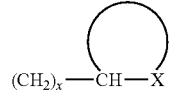

(β)

containing a saturated or unsaturated ring which may have 5 to 7 ring members and besides X 1 to 2 further heteroatoms selected from oxygen, sulfur and nitrogen and which ring may be substituted with 1 to 5 groups selected from $R^a$;

$R^a$ is each independently halogen, cyano, nitro, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, $C_3$-$C_8$-halocycloalkenyl, phenoxy, $OR^i$, $SR^i$, $S(=O)R^i$, $S(=O)_2R^i$, $NR^iR^j$, $-S(=O)_2NR^iR$, $C(=O)R^i$, $C(=O)OR^i$, $C(=O)NR^iR^j$, $C(=NOR^i)R^j$, $-NR^iC(=G)R^j$, $-N[C(=G)R^i]_2$, $-NR^iC(=G)OR^j$, $-C(=G)NR^i-NR^j{}_2$, $-NR^iSO_2R^j$, $SiR^i{}_yR^j{}_{3-y}$ (y is 0 to 3), or phenyl or a 5- to 6-membered heteroaromatic ring which contains 1 to 4 heteroatoms selected from oxygen, nitrogen and sulfur, wherein the carbon atoms in phenyl or in the heteroaromatic ring may be substituted with 1 to 5 halogens;

with the proviso that if X is oxygen, then $R^3$ is selected from halogen, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl or tri($C_1$-$C_{10}$)alkylsilyl;

G is oxygen or sulfur;

$R^i$, $R^j$ are each independently hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, or $C_3$-$C_6$-halocycloalkenyl; and Q is $C_1$-$C_{12}$-alkyl, $C_1$-$C_{12}$-haloalkyl, $C_2$-$C_7$-alkenyl, $C_2$-$C_7$-haloalkenyl, $C_2$-$C_7$-alkynyl, $C_2$-$C_7$-haloalkynyl, $C_3$-$C_7$-cycloalkyl, $C_3$-$C_7$-halocycloalkyl, $C_3$-$C_7$-cycloalkyl-$C_1$-$C_5$-alkyl, $C_3$-$C_7$-halocycloalkyl-$C_1$-$C_5$-alkyl, wherein each group is unsubstituted or substituted with one or more, preferably 1 to 3, groups $C_3$-$C_7$-cycloalkyl, $C_3$-$C_7$-halocycloalkyl or tri($C_1$-$C_{10}$)alkylsilyl;

and the enantiomers, diastereomers, salts, N-oxides and polymorphs thereof.

In addition, the invention provides processes and intermediates for preparing the compounds (I), pesticidal compositions comprising compounds (I), methods for the control of pests, e.g. harmful arthropods, like insects and arachnids, specifically insects and *Acarina*, and helminths, like nematodes, by contacting the pests or their food supply, habitat or breeding grounds with a pesticidally effective amount of compounds or compositions of formula (I).

Moreover, the invention provides a method of protecting growing plants from attack or infestation by pests by applying to the plants, or to the soil or water in which they are growing, a pesticidally effective amount of compositions or compounds of formula (I).

This invention also provides a method for treating, controlling, preventing or protecting animals against infestation or infection by parasitical pests, like helminths, specifically nematodes, which comprises orally, topically or parenterally administering or applying to the animals a parasiticidally effective amount of compositions or compounds of formula (I).

Compounds of formula (I) are obtainable, for example, by a process wherein a compound (II) is reacted with a compound (III) to give compounds (I):

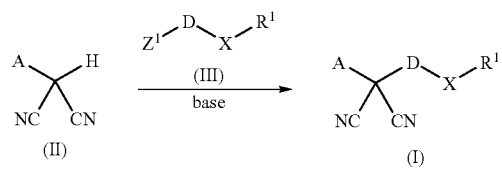

wherein A, D, X and $R^1$ are as defined above for compounds of formula (I) and $Z^1$ represents a suitable leaving group such as a halogen atom, methanesulfonate, trifluoromethanesulfonate or toluenesulfonate.

Of course one can also start from a compound (II)'

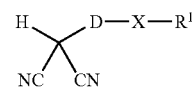

and react it with a compound (III)' $Z^1$-Q. The following applies correspondingly to reactions of compounds (II)' and (III)'.

The reaction is generally carried out in the presence of a base in a solvent.

The solvent to be used in the reaction includes, for example, acid amides such as N,N-dimethylformamide, NMP and the like, ethers such as diethyl ether, tetrahydrofuran and the like, sulfoxides and sulfones such as dimethylsulfoxide, sulfolane and the like, halogenated hydrocarbons such as 1,2-dichloroethane, chlorobenzene and the like, aromatic hydrocarbons such as toluene, xylene and the like, and mixtures thereof.

The base to be used in the reaction includes, for example, inorganic bases such as sodium hydride, sodium carbonate, potassium carbonate and the like, alkali metalalkoxides such as potassium t-butoxide and the like, alkali metal amides such as lithium diisopropylamide and the like, and organic bases such as dimethylaminopyridine, 1,4-diazabicyclo[2.2.2]octane, 1,8-diazabicyclo[5.4.0]-7-undecene and the like.

The amount of the base that can be used in the reaction is usually 1 to 10 moles relative to 1 mole of compound (II). In addition, additives such as crown ethers may be added to accelerate the reaction.

The amount of compound (III) to be used in the reaction is usually 1 to 10 moles, preferably 1 to 2 moles relative to 1 mole of compound (II).

The reaction temperature is usually in the range of −78° C. to 150° C., preferably in the range of −20° C. to 80° C. and the reaction time is usually in the range of 1 to 24 hours.

The compound (II) can be produced, for example, by reacting a compound (IV) with malononitrile:

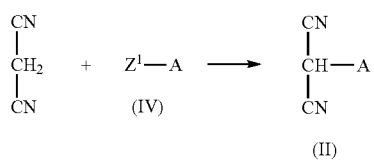

wherein A and $Z^1$ are as defined above.

The reaction is usually performed in a solvent in the presence of a base.

The solvent used in the reaction includes, for example, aliphatic hydrocarbons, such as hexane, heptane, octane or cyclohexane, aromatic hydrocarbons, such as toluene, xylene or mesitylene, ethers, such as diethyl ether, methyl tert-butyl ether, tetrahydrofuran or 1,4-dioxane, acid amides, such as N,N-dimethylformamide, and mixtures thereof.

The bases used in the reaction include, e.g., carbonates such as sodium carbonate or potassium carbonate, alkali metal hydrides, such as sodium hydride, and tertiary amines such as triethyl amine or diisopropylethylamine.

The amount of malononitrile used in the reaction is usually 0.5 to 10 moles, preferably 0.5 to 1 mole, per 1 mole of the compound (d). The amount of a base used in the reaction is usually 0.5 to 5 mmoles per 1 mole of the compound (d).

The reaction temperature is usually in the range of −20 to 100° C. The reaction time is usually in the range of 0.1 to 24 hours.

After completion of the reaction, the compound (II) can be isolated by subjecting the reaction mixture to customary work-up procedures, such as adding the reaction mixture to water, extracting with an organic solvent, concentrating the extract and the like. The isolated compound (II) may be purified by chromatography, recrystallization and the like, if necessary.

The compound (II) can be further produced, for example, according to the route represented by the following scheme:

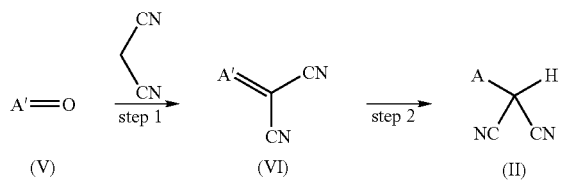

wherein A' is the respective "ylidene" rest of A and the other variables are as defined above for formula (I).

Analogously, this reaction can be carried out with a compound O=D'—X—R$^1$, where D' is the respective ylidene-rest of D.

Step 1: The compound (VI) can be produced by reacting compound (V) with malononitrile (CN(CH$_2$)CN; see e.g. Organic Process Research & Development 2005, 9, 133-136). The reaction is generally carried out in the presence of base in a solvent. The solvent to be used in the reaction includes, for example, acid amides such as N,N-dimethylformamide and the like, ethers such as diethyl ether, tetrahydrofuran and the like, halogenated hydrocarbons such as chloroform, 1,2-dichloroethane, chlorobenzene and the like, aromatic hydrocarbons such as toluene, xylene and the like, alcohols such as methanol, ethanol, isopropyl alcohol and the like, and mixtures thereof.

The base to be used in the reaction includes, for example, tetrabutylammonium hydroxide. The amount of the base that can be used in the reaction is usually 0.01 to 0.5 moles relative to 1 mole of compound (V).

The amount of malononitrile to be used in the reaction is usually 1 to 10 moles relative to 1 mole of compound (V). The reaction temperature is usually in the range of −20° C. to 200° C., and the reaction time is usually in the range of 1 to 24 hours.

The reaction may be carried out with removing the water formed by the reaction from the reaction system, if necessary.

After completion of the reaction, the compound of formula (VI) can be isolated by employing conventional methods such as adding the reaction mixture to water, extracting with an organic solvent, concentrating the extract and the like. The isolated compound (VI) can be purified by a technique such as chromatography, recrystallization and the like, if necessary.

Step 2: (a) If A is substituted by R$^2$, compound (II) can be produced by reacting compound (VI) with an organometallic compound R$^2$—U.

The reaction is generally carried out in a solvent, and if necessary, in the presence of a copper salt.

The solvent to be used in the reaction includes, for example, ethers such as diethyl ether, tetrahydrofuran and the like, aromatic hydrocarbons such as toluene, xylene and the like, and mixtures thereof.

The organometallic compound R$^2$—U to be used in the reaction includes, for example, organomagnesium compounds such as methylmagnesium iodide, ethylmagnesium bromide, isopropylmagnesium bromide, vinylmagnesium bromide, ethynylmagnesium bromide, dimethylmagnesium and the like, organolithium compounds such as methyllithium and the like, organozinc compounds such as diethylzinc and the like, and organocopper compounds such as trifluoromethylcopper and the like. The amount of the organometallic compound that can be used in the reaction is usually 1 to 10 moles relative to 1 mole of compound (VI).

The copper salt to be used in the reaction includes, for example, cuprous (1) iodide, cuprous (I) bromide and the like. The amount of the copper salt to be used in the reaction is usually not more than 1 mole relative to 1 mole of compound (VI). The reaction temperature is usually in the range of −20° C. to 100° C., and the reaction time is usually in the range of 1 to 24 hours.

After completion of the reaction, the compound of formula (II) can be isolated by employing conventional methods such as adding the reaction mixture to water, extracting with an organic solvent, concentrating the extract and the like. The isolated compound (II) can be purified by a technique such as chromatography, recrystallization and the like, if necessary.

Step 2: (b) If A is unsubstituted, the compound (II) can be produced by reacting compound (VI) with a reducing agent such as formic acid in the presence of a base as described e.g. in J. Org. Chem. 2005, 70, p. 3591, or with Mg in the presence of ZnCl2 as described in Synlett. 2005, p. 523-525 or any other suitable reducing agent.

After completion of the reaction, the compound of formula (II) can be isolated by employing conventional methods such as adding the reaction mixture to water, extracting with an organic solvent, concentrating the extract and the like. The isolated compound (II) can be purified by a technique such as chromatography, recrystallization and the like, if necessary.

In general, compounds (III), if not commercially available, can be synthesized from alcohols (VII) via conversion to the respective tosylates, mesylates or halides in analogy to methods mentioned in J. March, Advanced Organic Chemistry, 4$^{th}$ edition, Wiley.

Compounds (VII) can be obtained via alkylation of compounds (VIII) where Z$^2$ is a suitable leaving group such as a halogen atom, methanesulfonate, trifluoromethanesulfonate or toluenesulfonate, with compounds (IX) which are suitably substituted thiols or alcohols or salts thereof in analogy to procedures described in Can. J. Chem. 1979, 57, p. 1958-1966 and J. Am. Chem. Soc. 1924, 46, p. 1503.

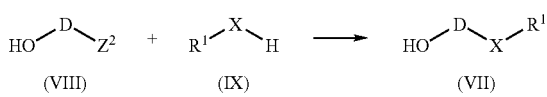

Specifically, compounds (III) wherein $R^1$ is $CF_3$, X is sulfur and $Z^1$ is halogen can also be obtained by reaction of $CF_3$—SH with acryl halides $CH_2CH$—$Z^1$ as described in J. Am. Chem. Soc. 1962, 84, p. 3148-3153.

Compounds (VIII) wherein $R^1$ is $CF_3$ and X is sulfur can be prepared for example by alkylation of mercapto alcohols HO-D-SH under irradiation conditions as described in WO 01/36410.

Compounds (III) wherein $R^1$ is $CF_3$ and X is oxygen can be obtained as described in J. Fluorine Chemistry 1982, 21, p. 133-143 or J. Org. Chem. 2001, 66, p. 1061-1063.

Symmetrical compounds of formula (I) in which A is D-X—$R^1$ and both groups D-X—$R^1$ are identical, can be produced by reacting two equivalents of a compound (III) with malononitrile:

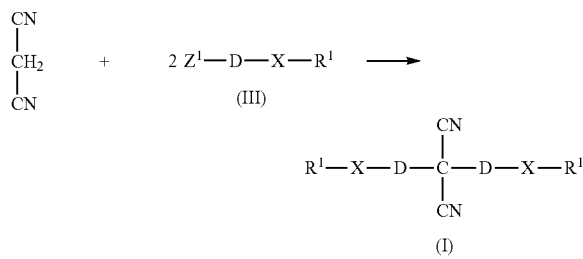

wherein $Z^1$ represents, e.g., chlorine, bromine, iodine, methanesulfonyloxy, toluenesulfonyloxy or trifluoromethanesulfonyloxy.

The reaction is usually performed in a solvent in the presence of a base.

The solvents used in the reaction include aliphatic hydrocarbons, such as hexane, heptane, octane or cyclohexane, aromatic hydrocarbons, such as toluene, xylene or mesitylene, ethers, such as diethyl ether, methyl tert-butyl ether, tetrahydrofuran or 1,4-dioxane, acid amides, such as N,N-dimethylformamide, dialkyl sulfoxides, such as dimethyl sulfoxide, and mixtures thereof.

The base used in the reaction includes carbonates, such as sodium carbonate or potassium carbonate, alkali metal hydrides, such as sodium hydride, and tertiary amines, such as triethylamine or diisopropylethylamine.

The amount of malononitrile used in the reaction is usually 0.3 to 1 moles per 1 mole of the compound (III). The amount of a base used in the reaction is usually 0.6 to 5 moles per 1 mole of the compound (III).

The reaction temperature is usually in the range of –20 to 100° C. The reaction time is usually in the range of 0.1 to 36 hours.

After completion of the reaction, the present compound can be isolated by subjecting the reaction mixture to post-treatment such as adding the reaction mixture into water, extracting with an organic solvent, concentrating the extract and the like. The isolated compound (I) can be purified by chromatography, recrystallization or the like, if necessary.

Compounds of formula (I) wherein D is a substituted or unsubstituted $C_1$-unit, the synthesis can be carried out by an addition reaction of a dinitrile (II) to a suitable carbonyl compound of formula D=O in analogy to procedures described in U.S. Pat. No. 4,581,178, J. Fluorine Chemistry 1982, 20, p. 397-418 and European Journal of Organic Chemistry 2004, (19), p. 3992-4002 and subsequent conversion of the obtained alcohols to compounds (I) via conversion of the OH-group of (VII) into a leaving group such as a mesylate-group and subsequent reaction with an alcohol or thiol $R^1$—XH, X=O or S, in analogy to a procedure in Eur. J. of Org. Chem. 2004, (19), 3992-4002.

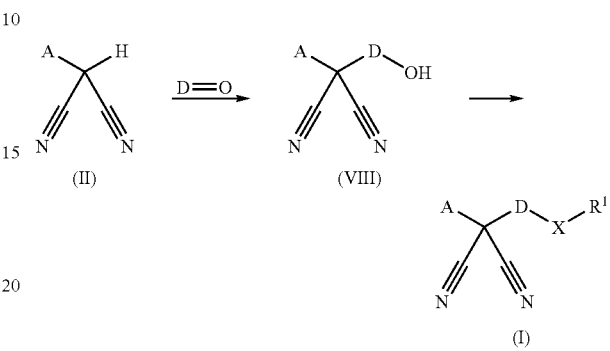

Compounds (I) of the invention wherein X is S and n is 1 can be obtained from the corresponding compounds (I) wherein X is S and n is 0 via oxidation with oxidizing agents such as 30% $H_2O_2$, $NaIO_4$ or t-BuOCl according to procedures described in J. March, Advanced Organic Chemistry, $4^{th}$ edition, Wiley, chapter 19, pp. 1201 and literature cited therein. Further oxidation with, for example, $KMnO_4$, $KHSO_5$ or another equivalent of 30% $H_2O_2$ as described in the literature cited above, yields compounds (I) wherein X is S and n is 2.

If individual compounds (I) are not obtainable by the routes described above, they can be prepared by derivatization of other compounds (I) or by customary modifications of the synthesis routes described.

After completion of the reaction, the compounds can be isolated by employing conventional methods such as adding the reaction mixture to water, extracting with an organic solvent, concentrating the extract and the like. The isolated compounds can be purified by a technique such as chromatography, recrystallization and the like, if necessary.

The preparation of the compounds of formula (I) may lead to them being obtained as isomer mixtures. If desired, these can be resolved by the methods customary for this purpose, such as crystallization or chromatography, also on optically active adsorbate, to give the pure isomers. The compounds of formula (I) may be present in different crystalline modifications (polymorphs) which may have different biological activity. These are also subject of the invention.

Agronomically acceptable salts of the compounds (I) can be formed in a customary manner, e.g. by reaction with an acid of the anion in question.

In this specification and in the claims, reference will be made to a number of terms that shall be defined to have the following meanings:

"Salt" as used herein includes adducts of compounds (I) with maleic acid, dimaleic acid, fumaric acid, difumaric acid, methane sulfenic acid, methane sulfonic acid, and succinic acid. Moreover, included as "salts" are those that can form with, for example, amines, metals, alkaline earth metal bases or quaternary ammonium bases, including zwitterions. Suitable metal and alkaline earth metal hydroxides as salt formers include the salts of barium, aluminum, nickel, copper, manganese, cobalt zinc, iron, silver, lithium, sodium, potassium, magnesium or calcium. Additional salt formers include chloride, sulfate, acetate, carbonate, hydride, and hydroxide. Desirable salts include adducts of compounds I with maleic acid, dimaleic acid, fumaric acid, difumaric acid, and methane sulfonic acid.

"Halogen" will be taken to mean fluoro, chloro, bromo and iodo.

The term "alkyl" as used herein refers to a branched or unbranched saturated hydrocarbon group having 1 to 6 carbon atoms, such as $C_1$-$C_6$-alkyl, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The term "haloalkyl" as used herein refers to a straight-chain or branched alkyl group having 1 to 6 carbon atoms (as mentioned above), where some or all of the hydrogen atoms in these groups are replaced by halogen atoms as mentioned above, for example $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl.

Similarly, "alkoxy" and "alkylthio" refer to straight-chain or branched alkyl groups having 1 to 6 carbon atoms (as mentioned above) bonded through oxygen or sulfur linkages, respectively, at any bond in the alkyl group. Examples include methoxy, ethoxy, propoxy, isopropoxy, methylthio, ethylthio, propylthio, isopropylthio, and n-butylthio.

Similarly, "alkylsulfinyl" and "alkylsulfonyl" refer to straight-chain or branched alkyl groups having 1 to 6 carbon atoms (as mentioned above) bonded through —S(=O)— or —S(=O)$_2$-linkages, respectively, at any bond in the alkyl group. Examples include methylsulfinyl and methylsulfonyl.

Similarly, "alkylamino" refers to a nitrogen atom which carries 1 or 2 straight-chain or branched alkyl groups having 1 to 6 carbon atoms (as mentioned above) which may be the same or different. Examples include methylamino, dimethylamino, ethylamino, diethylamino, methylethylamino, isopropylamino, or methylisopropylamino.

The term "alkylcarbonyl" refers to straight-chain or branched alkyl groups having 1 to 6 carbon atoms (as mentioned above) bonded through a —C(=O)— linkage, respectively, at any bond in the alkyl group. Examples include acetyl and propionyl.

The term "alkenyl" as used herein intends a branched or unbranched unsaturated hydrocarbon group having 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

The term "alkynyl" as used herein refers to a branched or unbranched unsaturated hydrocarbon group containing at least one triple bond, such as ethynyl, propynyl, 1-butynyl, 2-butynyl, and the like.

Cycloalkyl as used herein refers to monocyclic 3- to 6-membered saturated carbon atom rings, e.g. $C_3$-$C_6$-cycloalkyl such as cyclopropyl, cyclobutyl, cyclopentyl, or cyclohexyl.

A 5- or 6-membered heteroaromatic ring which contains 1 to 4 heteroatoms selected from oxygen, nitrogen and sulfur may be a 5-membered heteroaromatic ring containing 1 nitrogen atom and 0 to 2 further heteroatoms independently selected from oxygen, nitrogen and sulfur, preferably from oxygen and nitrogen, such as pyrrol, pyrazol, imidazol, triazol, oxazol, isoxazol, oxadiazol, thiazol, isothiazol, thiodiazol; or a 5-membered heteroaromatic ring containing 1 heteroatom selected from oxygen and sulfur, such as furane or thiophen; or a 6-membered heteroaromatic ring containing 1 nitrogen atom and 0 to 2 further heteroatoms independently selected from oxygen, nitrogen and sulfur, preferably from oxygen and nitrogen, such as pyridine, pyrazine, pyrimidine, pyridazine or triazine.

A 5- to 6-membered saturated, partially unsaturated or aromatic heterocyclic ring which contains 1 to 3 heteroatoms selected from oxygen, nitrogen and sulfur is e.g. pyridine, pyrimidine, (1,2,4)-oxadiazole, (1,3,4)-oxadiazole, pyrrole, furan, thiophene, oxazole, thiazole, imidazole, pyrazole, isoxazole, 1,2,4-triazole, tetrazole, pyrazine, pyridazine, oxazoline, thiazoline, tetrahydrofuran, tetrahydropyran, morpholine, piperidine, piperazine, pyrroline, pyrrolidine, oxazolidine, thiazolidine. Most preferably, this ring system is dioxolan, furan, oxazol, thiazol, or tetrahydrofuran.

A 5- or 6-membered heteroaromatic ring which contains 1 to 3 heteroatoms selected from oxygen, nitrogen and sulfur may be a 5-membered heteroaromatic ring containing 1 nitrogen atom and 0 to 2 further heteroatoms independently selected from oxygen, nitrogen and sulfur, such as pyrrol, pyrazol, imidazol, triazol, oxazol, isoxazol, oxadiazol, thiazol, isothiazol, thiodiazol; or a 5-membered heteroaromatic ring containing 1 heteroatom selected from oxygen and sulfur, such as furane or thiophen; or a 6-membered heteroaromatic ring containing 1 nitrogen atom and 0 to 2 further heteroatoms independently selected from oxygen, nitrogen and sulfur, preferably from nitrogen, such as pyridine, pyrazine, pyrimidine, pyridazine or triazine.

When fused to a 5- to 6-membered saturated, partially unsaturated or aromatic heterocyclic ring which contains 1 to 3 heteroatoms selected from oxygen, nitrogen and sulfur, this fused ring system is e.g. pyrimidotriazolyl.

A 3- to 7-membered saturated or partially unsaturated heterocyclic ring which contains 1 to 3 heteroatoms selected from oxygen, sulfur and nitrogen is e.g. a 5- to 7-membered heteroaromatic ring containing 1 nitrogen atom and 0 or 1 further heteroatoms independently selected from oxygen and nitrogen, such as morpholine, piperazine, piperidine, or pyrrolidine.

When fused to a 5- to 6-membered saturated, partially unsaturated or aromatic heterocyclic ring which contains 1 to 3 heteroatoms selected from oxygen, nitrogen and sulfur, this fused ring system is e.g. indoline.

Phenyl which is fused to phenyl or a 5- to 6-membered saturated, partially unsaturated or aromatic heterocyclic ring which contains 1 to 3 heteroatoms selected from oxygen, nitrogen and sulfur is e.g. naphthyl, benzoxazolyl, benzthiazolyl, benzimidazolyl, benzoxadiazolyl, or benzthiadiazolyl.

The saturated or unsaturated ring of formula α

(α)

which may have 5 to 7 ring members and besides X 1 to 2 further heteroatoms selected from oxygen, sulfur and nitrogen, e.g. is furanyl, thiophenyl, tetrahydrofuranyl, tetrahydrothiophenyl, tetrahydrothiophenyl oxide or tetrahydrothiophenyl dioxide.

The group of formula β

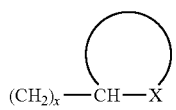

(β)

which contains a saturated or unsaturated ring which may have 5 to 7 ring members and besides X 1 to 2 further heteroatoms selected from oxygen, sulfur and nitrogen e.g. is —$CH_2$-furanyl, —$CH_2$-thiophenyl, —$CH_2$-tetrahydrofuranyl, —$CH_2$-tetrahydrothiophenyl, —$CH_2$-tetrahydrothiophenyl oxide, —$CH_2$-tetrahydrothiophenyl dioxide, —$(CH_2)_2$-furanyl, —$(CH_2)_2$-thiophenyl, —$(CH_2)_2$-tetrahydrofuranyl, —$(CH_2)_2$-tetrahydrothiophenyl, —$(CH_2)_2$-tetrahydrothiophenyl oxide or, —$(CH_2)_2$-tetrahydrothiophenyl dioxide. The variable x in group β preferably is 1 or 2.

With respect to the intended use of the compounds of formula (II), preference is given to the following compounds.

Compounds of formula (I), wherein A is Q.
Compounds of formula (I), wherein A is D-X—$R^1$.
Compounds of formula (I), wherein A is D-X—$R^1$ and both groups D-X—$R^1$ are identical.

With respect to the intended use of the compounds of formula (I), preference is further given to the following meanings of the substituents, in each case on their own or in combination. For the precursors of the inventive compounds, these preferred substituents or the preferred combination of substituents apply accordingly.

A compound of formula (I) wherein X is oxygen or sulfur.
A compound of formula (I) where X is $S(O)_n$ (n=0, 1 or 2).
A compound of formula (I) wherein X is sulfur (n=0).
A compound of formula (I) wherein is $C_1$-$C_6$-alkyl, $C_1$-$C_6$-haloalkyl or phenyl.
A compound of formula (I) wherein $R^1$ is $C_1$-$C_6$-alkyl, $C_1$-$C_6$-haloalkyl or phenyl, wherein these groups may be partially or fully halogenated and/or substituted with 1 to 3 groups selected from cyano, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, or $C_3$-$C_6$-haloalkynyloxy.

A compound of formula (I) wherein $R^1$ is $C_1$-$C_6$-alkyl, $C_1$-$C_6$-haloalkyl or phenyl, wherein these groups may be partially or fully halogenated and/or substituted with 1 to 3 groups selected from cyano, $C_1$-$C_6$-alkyl, $C_1$-$C_6$-haloalkyl, $C_1$-$C_6$-alkoxy or $C_1$-$C_6$-haloalkoxy.

A compound of formula (I) wherein $R^1$ has one of the preferred meanings for Q.

A compound of formula (I) wherein $R^1$ is $C_1$-$C_6$-fluoroalkyl.

A compound of formula (I) wherein $R^1$ is $C_1$-$C_{10}$-alkyl, $C_1$-$C_{10}$-haloalkyl, $C_2$-$C_6$-alkenyl, $C_2$-$C_6$-haloalkenyl, $C_2$-$C_{10}$-alkynyl, $C_3$-$C_{10}$-haloalkynyl, $C_3$-$C_{10}$-cycloalkyl, $C_3$-$C_{10}$-halocycloalkyl, $C_3$-$C_{10}$-cycloalkenyl or $C_3$-$C_{10}$-halocycloalkenyl.

A compound of formula (I) wherein D is a $C_1$-$C_3$-alkylene chain.

A compound of formula (I) wherein D is unsubstituted or is substituted by one or more groups $R^3$ selected from halogen, cyano, $C_1$-$C_{10}$-alkyl and $C_1$-$C_{10}$-haloalkyl, preferably from halogen.

A compound of formula (I) wherein R1 is $C_1$-$C_{10}$-alkyl or $C_1$-$C_{10}$-haloalkyl.

A compound of formula (I) wherein $R^1$ is $C_1$-$C_4$-perfluoroalkyl.

A compound of formula (I) wherein $R^1$ is $CF_3$.

A compound of formula (I) wherein D is a saturated or partially unsaturated hydrocarbon chain with 2 to 4 carbon chain atoms or cyclopropyl, preferably a saturated hydrocarbon chain with 2 to 4, more preferred 2 to 3, in particular 2, carbon chain atoms.

A compound of formula (I) wherein $R^2$ is halogen, cyano, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_1$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy or $C_3$-$C_6$-haloalkynyloxy, preferably halogen, cyano, $C_1$-$C_{10}$-alkyl, $C_1$-$C_{10}$-haloalkyl, $C_1$-$C_6$-alkoxy or $C_1$-$C_6$-haloalkoxy.

A compound of formula (I) wherein $R^3$ is halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy or $C_3$-$C_6$-haloalkynyloxy.

A compound of formula (I) wherein $R^3$ is halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_3$-$C_6$-haloalkynyl, $C_3$-$C_6$-cycloalkyl, halocycloalkyl, $C_3$-$C_6$-cycloalkenyl, $C_3$-$C_6$-halocycloalkenyl or tri($C_1$-$C_{10}$)alkylsilyl.

A compound of formula (I) wherein $R^3$ is halogen, cyano, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy or $C_1$-$C_6$-haloalkoxy.

A compound of formula (I) wherein $R^a$ is each independently halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $OR^i$, $SR^i$, $S(=O)R^i$, $S(=O)_2R^i$, —$S(=O)_2NR^iR^j$, $C(=O)OR^i$, $C(=O)NR^iR^j$, or phenyl or a 5- to 6-membered heteroaromatic ring which contains 1 to 4 heteroatoms selected from oxygen, nitrogen and sulfur.

A compound of formula (I) wherein $R^a$ is each independently halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl or $C_1$-$C_6$-alkoxy.

A compound of formula (I) in which Q is $C_1$-$C_6$ alkyl optionally substituted with one or more halogen.

A compound of the formula (I) in which Q is $C_2$ alkyl optionally substituted with one or more halogen.

A compound of the formula (I) in which Q is ethyl.

A compound of the formula (I) in which Q is monofluoroethyl.

A compound of the formula (I) in which Q is 1-fluoroethyl.

A compound of the formula (I) in which Q is 2-fluoroethyl.

A compound of the formula (I) in which Q is difluoroethyl.

A compound of the formula (I) in which Q is trifluoroethyl.

A compound of the formula (I) in which Q is 3,2,2-trifluoroethyl.

A compound of the formula (I) in which Q is monochloroethyl.

A compound of the formula (I) in which Q is dichloroethyl.

A compound of the formula (I) in which Q is monobromoethyl.

A compound of the formula (I) in which Q is $C_3$ alkyl optionally substituted with one or more halogen.

A compound of the formula (I) in which Q is propyl.

A compound of the formula (I) in which Q is 3-chloro-2-methylpropyl.

A compound of the formula (I) in which Q is 2-bromo-3,3,3-trifluoropropyl.

A compound of the formula (I) in which Q is 2-chloro-3,3,3-trifluoropropyl.

A compound of the formula (I) in which Q is 2,2-dimethylpropyl.

A compound of the formula (I) in which Q is 2-monochloropropyl.

A compound of the formula (I) in which Q is 3-monochloropropyl.

A compound of the formula (I) in which Q is 3-monobromopropyl.

A compound of the formula (I) in which Q is 2-monofluoropropyl.

A compound of the formula (I) in which Q is 3,3-difluoropropyl.

A compound of the formula (I) in which Q is 3,3,3-trifluoropropyl.

A compound of the formula (I) in which Q is 2,2,3,3-tetrafluoropropyl.

A compound of the formula (I) in which Q is 2,2,3,3,3-pentafluoropropyl.

A compound of the formula (I) in which Q is $C_4$ alkyl optionally substituted with one or more halogen.

A compound of the formula (I) in which Q is butyl.

A compound of the formula (I) in which Q is isobutyl.

A compound of the formula (I) in which Q is 4-chlorobutyl.

A compound of the formula (I) in which Q is 4-chloro-2-butyl.

A compound of the formula (I) in which Q is 4-fluorobutyl.

A compound of the formula (I) in which Q is 4-bromobutyl.

A compound of the formula (I) in which Q is 3-bromobutyl.

A compound of the formula (I) in which Q is 3,4-dichlorobutyl.

A compound of the formula (I) in which Q is 3,3-difluorobutyl.

A compound of the formula (I) in which Q is 4,4,4-trifluorobutyl.

A compound of the formula (I) in which Q is 3,3,4,4-tetrafluorobutyl.

A compound of the formula (I) in which Q is 3,3,4,4,4-pentafluorobutyl.

A compound of the formula (I) in which Q is 2,2,3,4,4,4-hexafluorobutyl.

A compound of the formula (I) in which Q is 2,2,3,3,3,4,4-heptafluorobutyl.

A compound of the formula (I) in which Q is 3,4-dichloro-3,4,4-trifluorobutyl.

A compound of the formula (I) in which Q is 3-chloro-4-bromo-3,4,4-trifluorobutyl.

A compound of the formula (I) in which Q is 4-bromo-3,3,4-tetrafluorobutyl.

A compound of the formula (I) in which Q is 3(trifluoromethyl)-3,4,4,4-tetrafluorobutyl.

A compound of the formula (I) in which Q is $C_5$ alkyl optionally substituted with one or more halogen.

A compound of the formula (I) in which Q is pentyl.

A compound of the formula (I) in which Q is isopentyl.

A compound of the formula (I) in which Q is fluoropentyl.

A compound of the formula (I) in which Q is chloropentyl.

A compound of the formula (I) in which Q is 3,3-difluoropentyl.

A compound of the formula (I) in which Q is 5,5-difluoropentyl.

A compound of the formula (I) in which Q is 5,5,5-trifluoropentyl.

A compound of the formula (I) in which Q is 5-bromo-4-chloro-4,5,5-trifluoropentyl.

A compound of the formula (I) in which Q is 5-bromo-4,4,5,5-tetrafluoropentyl.

A compound of the formula (I) in which Q is 4-(trifluoromethyl)-4,5,5,5-tetrafluoropentyl.

A compound of the formula (I) in which Q is 3,4,4,5,5,5-hexafluoropentyl.

A compound of the formula (I) in which Q is 4,4,5,5,5-pentafluoropentyl.

A compound of the formula (I) in which Q is 3,3,4,4,5,5-heptafluoropentyl.

A compound of the formula (I) in which Q is 2,2,3,3,4,4,5,5-octafluoropentyl.

A compound of the formula (I) in which Q is 2,2,3,3,4,4,5,5,5-nonafluoropentyl.

A compound of the formula (I) in which Q is $C_6$ alkyl optionally substituted with one or more halogen.

A compound of the formula (I) in which Q is hexyl.

A compound of the formula (I) in which Q is isohexyl.

A compound of the formula (I) in which Q is 6,6,6-trifluorohexyl.

A compound of the formula (I) in which Q is 4,4,5,5,6,6,6-heptafluorohexyl.

A compound of the formula (I) in which Q is 3,3,4,4,5,5,6,6-octafluorohexyl group.

A compound of the formula (I) in which Q is 3,3,4,4,5,5,6,6,6-nonafluorohexyl group.

A compound of the formula (I) in which Q is $C_7$ alkyl optionally substituted with one or more halogen.

A compound of the formula (I) in which Q is heptyl.

A compound of the formula (I) in which Q is isoheptyl.

A compound of the formula (I) in which Q is 7,7,7-trifluoroheptyl.

A compound of the formula (I) in which Q is 6,6,7,7,7-pentafluoroheptyl.

A compound of the formula (I) in which Q is 5,5,6,6,7,7,7-heptafluoroheptyl.

A compound of the formula (I) in which Q is 4,4,5,5,6,6,7,7-octafluoroheptyl.

A compound of the formula (I) in which Q is 4,4,5,5,6,6,7,7,7-nonafluoroheptyl.

A compound of the formula (I) in which Q is 2,2,3,3,4,4,5,5,6,6,7,7-dodecafluoroheptyl.

A compound of the formula (I) in which Q is $C_2$-$C_7$-alkenyl optionally substituted with one or more halogen.

A compound of the formula (I) in which Q is propenyl optionally substituted with one or more halogen.

A compound of the formula (I) in which Q is propenyl.

A compound of the formula (I) in which Q is 2-methylpropenyl.

A compound of the formula (I) in which Q is 2-butenyl.

A compound of the formula (I) in which Q is 3-butenyl.

A compound of the formula (I) in which Q is 3,4,4-trifluoro-3-butenyl.

A compound of the formula (I) in which Q is 2-pentenyl.

A compound of the formula (I) in which Q is 3-pentenyl.

A compound of the formula (I) in which Q is 4-methyl-3-pentenyl.

A compound of the formula (I) in which Q is 5,5,5-trifluoro-3-pentenyl.

A compound of the formula (I) in which Q is 4-pentenyl.

A compound of the formula (I) in which Q is 4,5,5-trifluoro-4-butenyl.

A compound of the formula (I) in which Q is $C_2$-$C_7$-alkynyl optionally substituted with one or more halogen.

A compound of the formula (I) in which Q is 2-propynyl.

A compound of the formula (I) in which Q is 2-butynyl.

A compound of the formula (I) in which Q is 3-methyl-4-butynyl.

A compound of the formula (I) in which Q is 4,4,4-trifluoro-2-butynyl.

A compound of the formula (I) in which Q is 3-butynyl.

A compound of the formula (I) in which Q is $C_3$-$C_7$ cycloalkyl optionally substituted with one or more halogen.

A compound of the formula (I) in which Q is cyclopropyl optionally substituted with one or more halogen.

A compound of the formula (I) in which Q is cyclopropyl.

A compound of the formula (I) in which Q is 2,2-dichlorocyclopropyl.

A compound of the formula (I) in which Q is cyclobutyl optionally substituted with one or more halogen.

A compound of the formula (I) in which Q is cyclobutyl.

A compound of the formula (I) in which Q is cyclopentyl optionally substituted with one or more halogen.

A compound of the formula (I) in which Q is cyclopentyl.

A compound of the formula (I) in which Q is cyclohexyl optionally substituted with one or more halogen.

A compound of the formula (I) in which Q is cyclohexyl.

A compound of the formula (I) in which Q is 4,4-difluorocyclohexyl.

A compound of the formula (I) in which Q is ($C_3$-$C_7$ cycloalkyl optionally substituted with one or more halogen) $C_1$-$C_4$ alkyl.

A compound of the formula (I) in which Q is cyclopropylmethyl optionally substituted with one or more halogen.

A compound of the formula (I) in which Q is cyclopropylmethyl.

A compound of the formula (I) in which Q is 2,2-dichlorocyclopropylmethyl.

A compound of the formula (I) in which Q is cyclobutylmethyl optionally substituted with one or more halogen.

A compound of the formula (I) in which Q is cyclobutylmethyl.

A compound of the formula (I) in which Q is cyclopentylmethyl optionally substituted with one or more halogen.

A compound of the formula (I) in which Q is cyclopentylmethyl.

A compound of the formula (I) in which Q is cyclohexylmethyl optionally substituted with one or more halogen.

A compound of the formula (I) in which Q is cyclohexylmethyl.

A compound of the formula (I) in which Q is 4,4-difluorocyclohexylmethyl.

A compound of the formula (I) in which Q is $C_5$-$C_7$ alkyl optionally substituted with one or more halogen.

A compound of the formula (I) in which Q is cyclopropylmethyl.

A compound of the formula (I) in which Q is cyclopentylmethyl.

A compound of the formula (I) in which Q is 2,2-difluorocyclopropylmethyl.

A compound of the formula (I) in which Q is 3,3-difluorocyclopentylmethyl.

A compound of the formula (I) in which Q is $C_5$-$C_7$ alkyl optionally substituted with one or more fluorine.

A compound of the formula (I) in which Q is $C_5$-$C_7$ alkyl having 6 to 8 fluorine atoms.

A compound of the formula (I) in which Q is $C_4$-$C_5$ alkyl optionally substituted with one or more halogen.

A compound of the formula (I) in which Q is $C_4$-$C_5$ alkyl optionally substituted with one or more fluorine.

A compound of the formula (I) in which Q is $C_4$-$C_5$ alkyl having 6 to 8 fluorine atoms.

A compound of the formula (I) in which Q is $C_5$ alkyl optionally substituted with one or more fluorine.

Preferred is a compound of formula (I) wherein

D is selected from —$CH_2$—, —$CH(CH_3)$—, —$CH(CF_3)$—, —$(CH_2)_2$—, cyclopropyl, —$CH_2C(CH_3)_2$—, —$CH(CH_3)CH_2$—, —$CH_2CH(CH_3)$—, or —$(CH_2)_4$—;

X is oxygen, sulfur, $S(=O)$ or $S(=O)_2$; and $R^1$ is $CH_3$, $CH_2CH_3$, $(CH_2)_2CH_3$, $CH(CH_3)_2$, $(CH_2)_2CH_3$, $CH_2CH(CH_3)_2$, $C(CH_3)_3$, phenyl, pentachlorophenyl, pentafluorophenyl, $CH_2CCH_2$, cyclopropyl, $CH_2CCH$, benzyl, $CF_3$, $CCl_3$, $CH_2CF_3$, $CH_2CHCCl_2$, $CF_2CF_3$, cyclopentyl, cyclohexyl, $CH_2CH(CF_3)_2$, or the moiety -D-X—$R^1$ together forms furanyl, tetrahydrofuranyl, thiophenyl, tetrahydrothiophenyl, tetrahydrothiophenyl oxide, tetrahydrothiophenyl dioxide, 3-$CF_3$-thiophen-1-yl, 3-$CF_3$-tetrahydrothiophen-1-yl, 3-$CF_3$-furan-1-yl, or 3-$CF_3$-tetrahydrofuran-1-yl.

More preferred is a compound of formula (I) wherein

D is selected from —$CH_2$—, —$CH(CH_3)$—, —$CH(CF_3)$—, —$(CH_2)_2$—, cyclopropyl, —$CH_2C(CH_3)_2$—, —$CH(CH_3)CH_2$—, —$CH_2CH(CH_3)$—, or —$(CH_2)_4$—;

X is oxygen, sulfur, $S(=O)$ or $S(=O)_2$; and $R^1$ is $CH_3$, $CH_2CH_3$, $(CH_2)_2CH_3$, $CH(CH_3)_2$, $(CH_2)_2CH_3$, $CH_2CH(CH_3)_2$, $C(CH_3)_3$, phenyl, pentachlorophenyl, pentafluorophenyl, $CH_2CHCH_2$, cyclopropyl, $CH_2CCH$, benzyl, $CF_3$, $CCl_3$, $CH_2CF_3$, $CH_2CHCCl_2$, $CF_2CF_3$, cyclopentyl, cyclohexyl, $CH_2CH(CF_3)_2$, or the moiety -D-X—$R^1$ together forms furanyl, tetrahydrofuranyl, thiophenyl, tetrahydrothiophenyl, tetrahydrothiophenyl oxide, tetrahydrothiophenyl dioxide, 3-$CF_3$-thiophen-1-yl, 3-$CF_3$-tetrahydrothiophen-1-yl, 3-$CF_3$-furan-1-yl, or 3-$CF_3$-tetrahydrofuran-1-yl.

More preferred is further a compound of formula (I) wherein

D is a saturated hydrocarbon chain with 2 to 4, more preferred 2 to 3, in particular 2, carbon chain atoms;

X is sulfur, and $R^1$ is $C_1$-$C_6$-fluoroalkyl, in particular $CF_3$, $CH_2$—$CF_3$, $CF_2$—$CF_3$ and $CF_2$—$CF_2H$.

Also preferred is a compound of formula (I) wherein
A is Q;
X is $S(O)_n$;
n is 0, 1 or 2;
$R^1$ is $C_1$-$C_{10}$-alkyl, $C_1$-$C_{10}$-haloalkyl, $C_2$-$C_6$-alkenyl, $C_2$-$C_6$-haloalkenyl, $C_2$-$C_{10}$-alkynyl, $C_3$-$C_{10}$-cycloalkyl, $C_3$-$C_{10}$-halocycloalkyl, $C_3$-$C_{10}$-cycloalkenyl or $C_3$-$C_{10}$-halocycloalkenyl, and
D is $C_1$-$C_3$-alkylene which is unsubstituted or is substituted by one or more groups selected from halogen, cyano, $C_1$-$C_{10}$-alkyl and $C_1$-$C_{10}$-haloalkyl.

More preferred is also a compound of formula (I) wherein
A is $C_1$-$C_{12}$-alkyl, $C_1$-$C_{12}$-haloalkyl, $C_2$-$C_6$-alkenyl, $C_2$-$C_6$-haloalkenyl, $C_3$-$C_7$-cycloalkyl, $C_3$-$C_7$-halocycloalkyl;
X is $S(O)_n$;
n is 0, 1 or 2;
R1 is $C_1$-$C_{10}$-alkyl or $C_1$-$C_{10}$-haloalkyl, and
D is C1-C3-alkylene, which is unsubstituted or substituted by halogen.

Especially preferred is a compound of formula (I) wherein
A is $C_1$-$C_{12}$-haloalkyl, $C_2$-$C_6$-haloalkenyl or $C_3$-$C_7$-cycloalkyl;
X is $S(O)_n$;
n is 0, 1 or 2;
R1 is $C_1$-$C_{10}$-haloalkyl and
D is $C_1$-$C_3$-alkylene.

Particularly preferred is a compound of formula (I) wherein the moiety Q is selected from table A.

TABLE A

| No. | Q |
|---|---|
| A-1 | $CH_2CH_2CH_2Cl$ |
| A-2 | $CH_2CH(CH_3)CH_2Cl$ |
| A-3 | $CH_2CH_2CH_2CH_2Cl$ |
| A-4 | 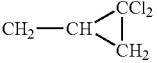 |
| A-5 | $CH_2CH_2CF_3$ |
| A-6 | $CH_2CH_3$ |
| A-7 | $CH_2CH_2CH_3$ |
| A-8 | $CH_2CH_2CH_2CH_3$ |
| A-9 | $CH_2CH_2CH_2CH_2CH_3$ |
| A-10 | $CH_2CH_2CH_2CH_2CH_2CH_3$ |
| A-11 | $CH_2CH_2CH_2CH_2CH_2CH_2CH_3$ |
| A-12 | $CH_2CH_2CH_2CH_2CH_2CH_2CH_2CH_3$ |
| A-13 | $CH_2CH_2CH_2CH_2CH_2CH_2CH_2CH_2CH_3$ |
| A-14 | $CH_2CH_2CH_2CH_2CH_2CH_2CH_2CH_2CH_2CH_3$ |
| A-15 | $CH_2CH=CH_2$ |
| A-16 | $CH_2CH_2CH=CH_2$ |
| A-17 | $CH_2CH_2CF=CF_2$ |
| A-18 | 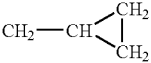 |
| A-19 | 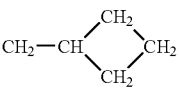 |
| A-20 | $CH_2CF_2CHF_2$ |
| A-21 | $CH_2CF_3$ |
| A-22 | $CH_2CF_2CF_3$ |
| A-23 | $CH_2CF_2CHFCF_3$ |
| A-24 | $CH_2CF_2CF_2CF_3$ |
| A-25 | $CH_2CH_2F$ |
| A-26 | $CH_2CH_2CF_2CF_2CF_2CF_2CF_2CF_3$ |
| A-27 | $CH_2C\equiv CH$ |
| A-28 | 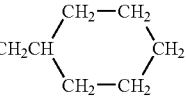 |
| A-29 | $CH_2CH_2CF_2CF_3$ |
| A-30 | $CH_2CH_2CFClCBrF_2$ |
| A-31 | $CH_2CF_2CF_2CF_2CHF_2$ |
| A-32 | $CH_2CF_2CF_2CF_2CF_2CHF_2$ |
| A-33 | $CH_2CF_2CF_2CF_2CF_2CF_2CF_2CF_2CF_2CF_2CF_2CF_3$ |
| A-34 | $CH_2CF_2CF_2CF_2CF_2CF_2CF_2CF_2CF_2CF_3$ |
| A-35 | $CH_2CH_2CF_2CBrF_2$ |
| A-36 | $CH_2CH_2CF(CF_3)_2$ |
| A-37 | $CH_2CH_2CF_2CF_3$ |
| A-38 | $CH_2CH_2CF_2CF_2CF_2CF_3$ |
| A-39 | $CH_2CH_2CH_2F$ |
| A-40 | $CH_2CH_2Br$ |
| A-41 | $CH_2CH_2CH_2Br$ |
| A-42 | $CH_2CH_2CH_2CH=CH_2$ |
| A-43 | $CH_2C(CH_3)_3$ |
| A-44 | $CH_2C(CH_3)=CH_2$ |
| A-45 | $CH_2CH(CH_3)_2$ |
| A-46 | $CH_2CH_2CFClCF_2Br$ |
| A-47 | $CH_2CH=CH_2$ |
| A-48 | $CH_2CH_2CH_2CF_3$ |
| A-49 | $CH_2CF_2CF_2CF_2CHF_2$ |
| A-50 | $CH_2CF_2CHF_2$ |
| A-51 | $CH_2CH_2CH_2CH_2CH_3$ |
| A-52 | $CH_2Br$ |
| A-53 | $CH_2CF_2CF_2CF_2CF_3$ |
| A-54 | $CH_2CH_2CFClCF_2Cl$ |
| A-55 | $CH_2CH_2CH_2CH_2CH_2F$ |
| A-56 | $CH_2CH_2CF(CF_3)_2$ |
| A-57 | $CH_2CHBrCF_3$ |
| A-58 | $CH_2CHClCF_3$ |
| A-59 | $CH_2CH_2CF_2CH_3$ |
| A-60 | $CH_2CH_2CF_3$ |
| A-61 | $CH_2CF_2CF_2H$ |
| A-62 | $CH_2CH_2CHBrCH_3$ |
| A-63 | $CH_2CH_2CH_2CH_2Br$ |
| A-64 | $CH_2CH_2CF_2CH_3$ |
| A-65 | $CH_2CH_2CH_2Br$ |
| A-66 | $CH_2CH_2CH_2CF_3$ |
| A-67 | $CH_2CH_2CFClCF_2Cl$ |
| A-68 | $CH_2CH_2CF_2CF_3$ |
| A-69 | $CH_2CHClCF_3$ |
| A-70 | $CH_2CH_2CF_2CH_2CH_3$ |
| A-71 | $CH_2CH_2CF_2CF_2CF_3$ |
| A-72 | 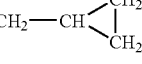 |
| A-73 | $CH_2CH_2CH=CH_2$ |
| A-74 | $CH_2CF_2CF_2CF_2CHF_2$ |
| A-75 | $CH_2CH_2CF=CF_2$ |
| A-76 | $CH_2C\equiv CH$ |
| A-77 | $CH_2CH_2CH(CH_3)_2$ |
| A-78 | $CH_2CH=C(CH_3)_2$ |
| A-79 | $CH_2CF_2CF_2CF_3$ |
| A-80 | $CH_2CH_2CH_2CH_3$ |
| A-81 | $CH_2CF_2CHFCF_3$ |
| A-82 | $CH_2CH_2CH_3$ |
| A-83 | 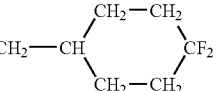 |
| A-84 | 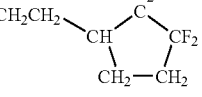 |

TABLE A-continued

| No. | Q |
|---|---|
| A-85 | cyclohexane with CH substituents bearing CH₂—CH₂ bridges and CF₃ (cis/trans = 5/1 mixture) |
| A-86 | cyclohexane with CH substituents bearing CH₂—CH₂ bridges and CH₃ (cis/trans = 2/1 mixture) |
| A-87 | cyclohexane with CH substituents bearing CH₂—CH₂ bridges, CH₂ and CHF₂ (cis form) |
| A-88 | cyclohexane with CH substituents bearing CH₂—CH₂ bridges, CH₂ and CH₂F (cis form) |
| A-89 | $CH_2CH_2CH_2CF_2CF_3$ |
| A-90 | $CH_2CH_2CH_2CF_2CH_3$ |
| A-91 | $CH_2CF_2CF_2CF_2CHF_2$ |
| A-92 | $CH_2CH_2CF_2CF_3$ |
| A-93 | $CH_2CF_2CF_3$ |
| A-94 | $CH_2CF_2CF=CF_2$ |
| A-95 | $CH_2CF_2CHFCF_3$ |
| A-96 | $CH_2CH_2CH=CF_2$ |
| A-97 | $CH_2(CF_2)_4CF_2H$ |
| A-98 | $CH_2(CF_2)_4CF_3$ |

Further particularly preferred is a compound of formula (I) wherein the moiety D-X—R¹ is selected from Table B.

TABLE B

| No. | D—X—R¹ |
|---|---|
| B-1 | $CH_2CH_2SCF_3$ |
| B-2 | $CH_2CH_2CH_2SCF_3$ |
| B-3 | $CH_2SCF_3$ |
| B-4 | $CH_2CH_2SCHF_2$ |
| B-5 | $CH_2CH_2CH_2SCHF_2$ |
| B-6 | $CH_2SCHF_2$ |
| B-7 | $CH_2CH_2SCF_2Cl$ |
| B-8 | $CH_2CH_2CH_2SCF_2Cl$ |
| B-9 | $CH_2SCF_2Cl$ |
| B-10 | $CH_2CH_2SCFCl_2$ |
| B-11 | $CH_2CH_2CH_2SCFCl_2$ |
| B-12 | $CH_2SCFCl_2$ |
| B-13 | $CH_2CH_2SCCl_3$ |
| B-14 | $CH_2CH_2CH_2SCCl_3$ |
| B-15 | $CH_2SCCl_3$ |
| B-16 | $CH_2CH_2SCH_3$ |
| B-17 | $CH_2CH_2CH_2SCH_3$ |
| B-18 | $CH_2SCH_3$ |
| B-19 | $CH_2CH_2SCH_2CF_3$ |
| B-20 | $CH_2CH_2CH_2SCH_2CF_3$ |
| B-21 | $CH_2SCH_2CF_3$ |
| B-22 | $CH_2CH_2SCF_2CF_3$ |
| B-23 | $CH_2CH_2CH_2SCF_2CF_3$ |
| B-24 | $CH_2SCF_2CF_3$ |
| B-25 | $CH_2CH_2SCF_2CHF_2$ |
| B-26 | $CH_2CH_2CH_2SCF_2CHF_2$ |
| B-27 | $CH_2SCF_2CHF_2$ |
| B-28 | $CH_2CH_2SCH_2CH_3$ |
| B-29 | $CH_2CH_2CH_2SCH_2CH_3$ |
| B-30 | $CH_2SCH_2CH_3$ |
| B-31 | $CH_2CH_2SCF_2CF_2OCH_3$ |
| B-32 | $CH_2CH_2CH_2SCF_2CF_2OCH_3$ |
| B-33 | $CH_2SCF_2CF_2OCH_3$ |
| B-34 | $CH_2CH_2SCF_2CF_2OCF_3$ |
| B-35 | $CH_2CH_2CH_2SCF_2CF_2OCF_3$ |
| B-36 | $CH_2SCF_2CF_2OCF_3$ |
| B-37 | $CH_2CH_2SCH_2CH_2CH_3$ |
| B-38 | $CH_2CH_2CH_2SCH_2CH_2CH_3$ |
| B-39 | $CH_2SCH_2CH_2CH_3$ |
| B-40 | $CH_2CH_2SCF_2CF_2CF_3$ |
| B-41 | $CH_2CH_2CH_2SCF_2CF_2CF_3$ |
| B-42 | $CH_2SCF_2CF_2CF_3$ |
| B-43 | $CH_2CH_2SCF_2CF_2CF_2H$ |
| B-44 | $CH_2CH_2CH_2SCF_2CF_2CF_2H$ |
| B-45 | $CH_2SCF_2CF_2CF_2H$ |
| B-46 | $CH_2CH_2SCH(CH_3)_2$ |
| B-47 | $CH_2CH_2CH_2SCH(CH_3)_2$ |
| B-48 | $CH_2SCH(CH_3)_2$ |
| B-49 | $CH_2CH_2SCH(CF_3)_2$ |
| B-50 | $CH_2CH_2CH_2SCH(CF_3)_2$ |
| B-51 | $CH_2SCH(CF_3)_2$ |
| B-52 | $CH_2CH_2SCF(CF_3)_2$ |
| B-53 | $CH_2CH_2CH_2SCF(CF_3)_2$ |
| B-54 | $CH_2SCF(CF_3)_2$ |
| B-55 | $CH_2CH_2SC(CH_3)_3$ |
| B-56 | $CH_2CH_2CH_2SC(CH_3)_3$ |
| B-57 | $CH_2SC(CH_3)_3$ |
| B-58 | $CH_2CH_2SCH_2CH_2CH_3$ |
| B-59 | $CH_2CH_2CH_2SCH_2CH_2CH_3$ |
| B-60 | $CH_2SCH_2CH_2CH_3$ |
| B-61 | $CH_2CH_2SCF_2CF_2CF_2H$ |
| B-62 | $CH_2CH_2CH_2SCF_2CF_2CF_2H$ |
| B-63 | $CH_2SCF_2CF_2CF_2H$ |
| B-64 | $CH_2CH_2SCF_2CF_2CF_3$ |
| B-65 | $CH_2CH_2CH_2SCF_2CF_2CF_3$ |
| B-66 | $CH_2SCF_2CF_2CF_3$ |
| B-67 | $CH_2CH_2SCH_2C_6H_5$ |
| B-68 | $CH_2CH_2CH_2SCH_2C_6H_5$ |
| B-69 | $CH_2SCH_2C_6H_5$ |
| B-70 | $CH_2CH_2SCH_2C_6F_5$ |
| B-71 | $CH_2CH_2CH_2SCH_2C_6F_5$ |
| B-72 | $CH_2SCH_2C_6F_5$ |
| B-73 | $CH_2CH(CH_3)SCF_3$ |
| B-74 | $CH_2CH_2CH(CH_3)SCF_3$ |
| B-75 | $CH(CH_3)SCF_3$ |
| B-76 | $CH(CH_3)CH_2SCF_3$ |
| B-77 | $CH(CH_3)CH_2CH_2SCF_3$ |
| B-78 | $CH(CH_3)CH_2SCF_3$ |
| B-79 | $CH_2CH(CH_3)SCF_2CF_3$ |
| B-80 | $CH_2CH_2CH(CH_3)SCF_2CF_3$ |
| B-81 | $CH(CH_3)SCF_2CF_3$ |
| B-82 | $CH(CH_3)CH_2SCF_2CF_3$ |
| B-83 | $CH(CH_3)CH_2CH_2SCF_2CF_3$ |
| B-84 | $CH_2CH(CH_3)CH_2SCF_2CF_3$ |
| B-85 | $CH_2CH(CH_3)SCF_2CHF_2$ |
| B-86 | $CH_2CH_2CH(CH_3)SCF_2CHF_2$ |
| B-87 | $CH(CH_3)SCF_2CHF_2$ |
| B-88 | $CH(CH_3)CH_2SCF_2CHF_2$ |
| B-89 | $CH(CH_3)CH_2CH_2SCF_2CHF_2$ |
| B-90 | $CH_2CH(CH_3)CH_2SCF_2CHF_2$ |
| B-91 | $CH_2CH(CH_3)SCH_2CF_3$ |
| B-92 | $CH_2CH_2CH(CH_3)SCH_2CF_3$ |
| B-93 | $CH(CH_3)SCH_2CF_3$ |
| B-94 | $CH(CH_3)CH_2SCH_2CF_3$ |
| B-95 | $CH(CH_3)CH_2CH_2SCH_2CF_3$ |
| B-96 | $CH_2CH(CH_3)CH_2SCH_2CF_3$ |
| B-97 | $CH_2CH(CH_3)SCF_2CF_3$ |
| B-98 | $CH_2CH_2CH(CH_3)SCF_2CF_3$ |
| B-99 | $CH(CH_3)SCF_2CF_3$ |
| B-100 | $CH(CH_3)CH_2SCF_2CF_3$ |
| B-101 | $CH(CH_3)CH_2CH_2SCF_2CF_3$ |
| B-102 | $CH_2CH(CH_3)CH_2SCF_2CF_3$ |
| B-103 | $CH(CH_3)SCF_2CF_2CHF_2$ |
| B-104 | $CH_2CH(CH_3)SCF_2CF_2CHF_2$ |

TABLE B-continued

| No. | D—X—R$^1$ |
|---|---|
| B-105 | CH(CH$_3$)SCF$_2$CF$_2$CHF$_2$ |
| B-106 | CH(CH$_3$)CH$_2$SCF$_2$CF$_2$CHF$_2$ |
| B-107 | CH(CH$_3$)CH$_2$CH$_2$SCF$_2$CF$_2$CHF$_2$ |
| B-108 | CH$_2$CH(CH$_3$)CH$_2$SCF$_2$CF$_2$CHF$_2$ |
| B-109 | CH$_2$OCF$_3$ |
| B-110 | CH$_2$CH$_2$OCF$_3$ |
| B-111 | CH$_2$CH$_2$CH$_2$OCF$_3$ |
| B-112 | CH$_2$OCF$_2$CF$_3$ |
| B-113 | CH$_2$CH$_2$OCF$_2$CF$_3$ |
| B-114 | CH$_2$CH$_2$CH$_2$OCF$_2$CF$_3$ |
| B-115 | CH$_2$OCF$_2$CHF$_2$ |
| B-116 | CH$_2$CH$_2$OCF$_2$CHF$_2$ |
| B-117 | CH$_2$CH$_2$CH$_2$OCF$_2$CHF$_2$ |
| B-118 | CH$_2$OCF(CF$_3$)$_2$ |
| B-119 | CH$_2$CH$_2$OCF(CF$_3$)$_2$ |
| B-120 | CH$_2$CH$_2$CH$_2$OCF(CF$_3$)$_2$ |
| B-121 | CH$_2$OCH(CF$_3$)$_2$ |
| B-122 | CH$_2$CH$_2$OCH(CF$_3$)$_2$ |
| B-123 | CH$_2$CH$_2$CH$_2$OCH(CF$_3$)$_2$ |
| B-124 | CH$_2$OC(CH$_3$)$_3$ |
| B-125 | CH$_2$CH$_2$OC(CH$_3$)$_3$ |
| B-126 | CH$_2$CH$_2$CH$_2$OC(CH$_3$)$_3$ |
| B-127 | CH$_2$OCH(CH$_3$)$_2$ |
| B-128 | CH$_2$CH$_2$OCH(CH$_3$)$_2$ |
| B-129 | CH$_2$CH$_2$CH$_2$OCH(CH$_3$)$_2$ |
| B-130 | CH$_2$S(O)CF$_3$ |
| B-131 | CH$_2$CH$_2$S(O)CF$_3$ |
| B-132 | CH$_2$CH$_2$CH$_2$S(O)CF$_3$ |
| B-133 | CH$_2$S(O)CF$_2$CF$_3$ |
| B-134 | CH$_2$CH$_2$S(O)CF$_2$CF$_3$ |
| B-135 | CH$_2$CH$_2$CH$_2$S(O)CF$_2$CF$_3$ |
| B-136 | CH$_2$S(O)CF$_2$CHF$_2$ |
| B-137 | CH$_2$CH$_2$S(O)CF$_2$CHF$_2$ |
| B-138 | CH$_2$CH$_2$CH$_2$S(O)CF$_2$CHF$_2$ |
| B-139 | CH$_2$S(O)CH(CF$_3$)$_2$ |
| B-140 | CH$_2$CH$_2$S(O)CH(CF$_3$)$_2$ |
| B-141 | CH$_2$CH$_2$CH$_2$S(O)CH(CF$_3$)$_2$ |
| B-142 | CH$_2$S(O)CF(CF$_3$)$_2$ |
| B-143 | CH$_2$CH$_2$S(O)CF(CF$_3$)$_2$ |
| B-144 | CH$_2$CH$_2$CH$_2$S(O)CF(CF$_3$)$_2$ |
| B-145 | CH$_2$S(O)C(CH$_3$)$_3$ |
| B-146 | CH$_2$CH$_2$S(O)C(CH$_3$)$_3$ |
| B-147 | CH$_2$CH$_2$CH$_2$S(O)C(CH$_3$)$_3$ |
| B-148 | CH$_2$S(O)CH(CH$_3$)$_2$ |
| B-149 | CH$_2$CH$_2$S(O)CH(CH$_3$)$_2$ |
| B-150 | CH$_2$CH$_2$CH$_2$S(O)CH(CH$_3$)$_2$ |
| B-151 | CH$_2$S(O)$_2$CF$_3$ |
| B-152 | CH$_2$CH$_2$S(O)$_2$CF$_3$ |
| B-153 | CH$_2$CH$_2$CH$_2$S(O)$_2$CF$_3$ |
| B-154 | CH$_2$S(O)$_2$CF$_2$CF$_3$ |
| B-155 | CH$_2$CH$_2$S(O)$_2$CF$_2$CF$_3$ |
| B-156 | CH$_2$CH$_2$CH$_2$S(O)$_2$CF$_2$CF$_3$ |
| B-157 | CH$_2$S(O)$_2$CF$_2$CHF$_2$ |
| B-158 | CH$_2$CH$_2$S(O)$_2$CF$_2$CHF$_2$ |
| B-159 | CH$_2$CH$_2$CH$_2$S(O)$_2$CF$_2$CHF$_2$ |
| B-160 | CH$_2$S(O)$_2$CH(CF$_3$)$_2$ |
| B-161 | CH$_2$CH$_2$S(O)$_2$CH(CF$_3$)$_2$ |
| B-162 | CH$_2$CH$_2$CH$_2$S(O)$_2$CH(CF$_3$)$_2$ |
| B-163 | CH$_2$S(O)$_2$CF(CF$_3$)$_2$ |
| B-164 | CH$_2$CH$_2$S(O)$_2$CF(CF$_3$)$_2$ |
| B-165 | CH$_2$CH$_2$CH$_2$S(O)$_2$CF(CF$_3$)$_2$ |
| B-166 | CH$_2$S(O)$_2$C(CH$_3$)$_3$ |
| B-167 | CH$_2$CH$_2$S(O)$_2$C(CH$_3$)$_3$ |
| B-168 | CH$_2$CH$_2$CH$_2$S(O)$_2$C(CH$_3$)$_3$ |
| B-169 | CH$_2$S(O)$_2$CH(CH$_3$)$_2$ |
| B-170 | CH$_2$CH$_2$S(O)$_2$CH(CH$_3$)$_2$ |
| B-171 | CH$_2$CH$_2$CH$_2$S(O)$_2$CH(CH$_3$)$_2$ |

With respect to their use, particular preference is given to the compounds (I-I) compiled in the tables below. Moreover, the groups mentioned for a substituent in the tables are on their own, independently of the combination in which they are mentioned, a particularly preferred embodiment of the substituent in question.

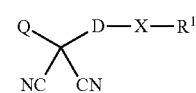

(I-1)

Table 1
Compounds of the formula (I-I), wherein Q denotes A-1, and D-X—R$^1$ corresponds in each case to a row of Table B.

Table 2
Compounds of the formula (I-I), wherein Q denotes A-2, and D-X—R$^1$ corresponds in each case to a row of Table B.

Table 3
Compounds of the formula (I-I), wherein Q denotes A-3, and D-X—R$^1$ corresponds in each case to a row of Table B.

Table 4
Compounds of the formula (I-I), wherein Q denotes A-4, and D-X—R$^1$ corresponds in each case to a row of Table B.

Table 5
Compounds of the formula (I-I), wherein Q denotes A-5, and D-X—R$^1$ corresponds in each case to a row of Table B.

Table 6
Compounds of the formula (I-I), wherein Q denotes A-6, and D-X—R$^1$ corresponds in each case to a row of Table B.

Table 7
Compounds of the formula (I-I), wherein Q denotes A-7, and D-X—R$^1$ corresponds in each case to a row of Table B.

Table 8
Compounds of the formula (I-I), wherein Q denotes A-8, and D-X—R$^1$ corresponds in each case to a row of Table B.

Table 9
Compounds of the formula (I-I), wherein Q denotes A-9, and D-X—R$^1$ corresponds in each case to a row of Table B.

Table 10
Compounds of the formula (I-I), wherein Q denotes A-10, and D-X—R$^1$ corresponds in each case to a row of Table B.

Table 11
Compounds of the formula (I-I), wherein Q denotes A-11, and D-X—R$^1$ corresponds in each case to a row of Table B.

Table 12
Compounds of the formula (I-I), wherein Q denotes A-12, and D-X—R$^1$ corresponds in each case to a row of Table B.

Table 13
Compounds of the formula (I-I), wherein Q denotes A-13, and D-X—R$^1$ corresponds in each case to a row of Table B.

Table 14
Compounds of the formula (I-I), wherein Q denotes A-14, and D-X—R$^1$ corresponds in each case to a row of Table B.

Table 15
Compounds of the formula (I-I), wherein Q denotes A-15, and D-X—R$^1$ corresponds in each case to a row of Table B.

Table 16
Compounds of the formula (I-I), wherein Q denotes A-16, and D-X—R$^1$ corresponds in each case to a row of Table B.

Table 17
Compounds of the formula (I-I), wherein Q denotes A-17, and D-X—R$^1$ corresponds in each case to a row of Table B.

Table 18
Compounds of the formula (I-I), wherein Q denotes A-18, and D-X—R$^1$ corresponds in each case to a row of Table B.

Table 19
Compounds of the formula (I-I), wherein Q denotes A-19, and D-X—R$^1$ corresponds in each case to a row of Table B.

Table 20
Compounds of the formula (I-I), wherein Q denotes A-20, and D-X—R$^1$ corresponds in each case to a row of Table B.

Table 21
Compounds of the formula (I-I), wherein Q denotes A-21, and D-X—$R^1$ corresponds in each case to a row of Table B.

Table 22
Compounds of the formula (I-I), wherein Q denotes A-22, and D-X—$R^1$ corresponds in each case to a row of Table B.

Table 23
Compounds of the formula (I-I), wherein Q denotes A-23, and D-X—$R^1$ corresponds in each case to a row of Table B.

Table 24
Compounds of the formula (I-I), wherein Q denotes A-24, and D-X—$R^1$ corresponds in each case to a row of Table B.

Table 25
Compounds of the formula (I-I), wherein Q denotes A-25, and D-X—$R^1$ corresponds in each case to a row of Table B.

Table 26
Compounds of the formula (I-I), wherein Q denotes A-26, and D-X—$R^1$ corresponds in each case to a row of Table B.

Table 27
Compounds of the formula (I-I), wherein Q denotes A-27, and D-X—$R^1$ corresponds in each case to a row of Table B.

Table 28
Compounds of the formula (I-I), wherein Q denotes A-28, and D-X—$R^1$ corresponds in each case to a row of Table B.

Table 29
Compounds of the formula (I-I), wherein Q denotes A-29, and D-X—$R^1$ corresponds in each case to a row of Table B.

Table 30
Compounds of the formula (I-I), wherein Q denotes A-30, and D-X—$R^1$ corresponds in each case to a row of Table B.

Table 31
Compounds of the formula (I-I), wherein Q denotes A-31, and D-X—$R^1$ corresponds in each case to a row of Table B.

Table 32
Compounds of the formula (I-I), wherein Q denotes A-32, and D-X—$R^1$ corresponds in each case to a row of Table B.

Table 33
Compounds of the formula (I-I), wherein Q denotes A-33, and D-X—$R^1$ corresponds in each case to a row of Table B.

Table 34
Compounds of the formula (I-I), wherein Q denotes A-34, and D-X—$R^1$ corresponds in each case to a row of Table B.

Table 35
Compounds of the formula (I-I), wherein Q denotes A-35, and D-X—$R^1$ corresponds in each case to a row of Table B.

Table 36
Compounds of the formula (I-I), wherein Q denotes A-36, and D-X—$R^1$ corresponds in each case to a row of Table B.

Table 37
Compounds of the formula (I-I), wherein Q denotes A-37, and D-X—$R^1$ corresponds in each case to a row of Table B.

Table 38
Compounds of the formula (I-I), wherein Q denotes A-38, and D-X—$R^1$ corresponds in each case to a row of Table B.

Table 39
Compounds of the formula (I-I), wherein Q denotes A-39, and D-X—$R^1$ corresponds in each case to a row of Table B.

Table 40
Compounds of the formula (I-I), wherein Q denotes A-40, and D-X—$R^1$ corresponds in each case to a row of Table B.

Table 41
Compounds of the formula (I-I), wherein Q denotes A-41, and D-X—$R^1$ corresponds in each case to a row of Table B.

Table 42
Compounds of the formula (I-I), wherein Q denotes A-42, and D-X—$R^1$ corresponds in each case to a row of Table B.

Table 43
Compounds of the formula (I-I), wherein Q denotes A-43, and D-X—$R^1$ corresponds in each case to a row of Table B.

Table 44
Compounds of the formula (I-I), wherein Q denotes A-44, and D-X—$R^1$ corresponds in each case to a row of Table B.

Table 45
Compounds of the formula (I-I), wherein Q denotes A-45, and D-X—$R^1$ corresponds in each case to a row of Table B.

Table 46
Compounds of the formula (I-I), wherein Q denotes A-46, and D-X—$R^1$ corresponds in each case to a row of Table B.

Table 47
Compounds of the formula (I-I), wherein Q denotes A-47, and D-X—$R^1$ corresponds in each case to a row of Table B.

Table 48
Compounds of the formula (I-I), wherein Q denotes A-48, and D-X—$R^1$ corresponds in each case to a row of Table B.

Table 49
Compounds of the formula (I-I), wherein Q denotes A-49, and D-X—$R^1$ corresponds in each case to a row of Table B.

Table 50
Compounds of the formula (I-I), wherein Q denotes A-50, and D-X—$R^1$ corresponds in each case to a row of Table B.

Table 51
Compounds of the formula (I-I), wherein Q denotes A-51, and D-X—$R^1$ corresponds in each case to a row of Table B.

Table 52
Compounds of the formula (I-I), wherein Q denotes A-52, and D-X—$R^1$ corresponds in each case to a row of Table B.

Table 53
Compounds of the formula (I-I), wherein Q denotes A-53, and D-X—$R^1$ corresponds in each case to a row of Table B.

Table 54
Compounds of the formula (I-I), wherein Q denotes A-54, and D-X—$R^1$ corresponds in each case to a row of Table B.

Table 55
Compounds of the formula (I-I), wherein Q denotes A-55, and D-X—$R^1$ corresponds in each case to a row of Table B.

Table 56
Compounds of the formula (I-I), wherein Q denotes A-56, and D-X—$R^1$ corresponds in each case to a row of Table B.

Table 57
Compounds of the formula (I-I), wherein Q denotes A-57, and D-X—$R^1$ corresponds in each case to a row of Table B.

Table 58
Compounds of the formula (I-I), wherein Q denotes A-58, and D-X—$R^1$ corresponds in each case to a row of Table B.

Table 59
Compounds of the formula (I-I), wherein Q denotes A-59, and D-X—$R^1$ corresponds in each case to a row of Table B.

Table 60
Compounds of the formula (I-I), wherein Q denotes A-60, and D-X—$R^1$ corresponds in each case to a row of Table B.

Table 61
Compounds of the formula (I-I), wherein Q denotes A-61, and D-X—$R^1$ corresponds in each case to a row of Table B.

Table 62
Compounds of the formula (I-I), wherein Q denotes A-62, and D-X—$R^1$ corresponds in each case to a row of Table B.

Table 63
Compounds of the formula (I-I), wherein Q denotes A-63, and D-X—$R^1$ corresponds in each case to a row of Table B.

Table 64
Compounds of the formula (I-I), wherein Q denotes A-64, and D-X—$R^1$ corresponds in each case to a row of Table B.

Table 65
Compounds of the formula (I-I), wherein Q denotes A-65, and D-X—R$^1$ corresponds in each case to a row of Table B.
Table 66
Compounds of the formula (I-I), wherein Q denotes A-66, and D-X—R$^1$ corresponds in each case to a row of Table B.
Table 67
Compounds of the formula (I-I), wherein Q denotes A-67, and D-X—R$^1$ corresponds in each case to a row of Table B.
Table 68
Compounds of the formula (I-I), wherein Q denotes A-68, and D-X—R$^1$ corresponds in each case to a row of Table B.
Table 69
Compounds of the formula (I-I), wherein Q denotes A-69, and D-X—R$^1$ corresponds in each case to a row of Table B.
Table 70
Compounds of the formula (I-I), wherein Q denotes A-70, and D-X—R$^1$ corresponds in each case to a row of Table B.
Table 71
Compounds of the formula (I-I), wherein Q denotes A-71, and D-X—R$^1$ corresponds in each case to a row of Table B.
Table 72
Compounds of the formula (I-I), wherein Q denotes A-72, and D-X—R$^1$ corresponds in each case to a row of Table B.
Table 73
Compounds of the formula (I-I), wherein Q denotes A-73, and D-X—R$^1$ corresponds in each case to a row of Table B.
Table 74
Compounds of the formula (I-I), wherein Q denotes A-74, and D-X—R$^1$ corresponds in each case to a row of Table B.
Table 75
Compounds of the formula (I-I), wherein Q denotes A-75, and D-X—R$^1$ corresponds in each case to a row of Table B.
Table 76
Compounds of the formula (I-I), wherein Q denotes A-76, and D-X—R$^1$ corresponds in each case to a row of Table B.
Table 77
Compounds of the formula (I-I), wherein Q denotes A-77, and D-X—R$^1$ corresponds in each case to a row of Table B.
Table 78
Compounds of the formula (I-I), wherein Q denotes A-78, and D-X—R$^1$ corresponds in each case to a row of Table B.
Table 79
Compounds of the formula (I-I), wherein Q denotes A-79, and D-X—R$^1$ corresponds in each case to a row of Table B.
Table 80
Compounds of the formula (I-I), wherein Q denotes A-80, and D-X—R$^1$ corresponds in each case to a row of Table B.
Table 81
Compounds of the formula (I-I), wherein Q denotes A-81, and D-X—R$^1$ corresponds in each case to a row of Table B.
Table 82
Compounds of the formula (I-I), wherein Q denotes A-82, and D-X—R$^1$ corresponds in each case to a row of Table B.
Table 83
Compounds of the formula (I-I), wherein Q denotes A-83, and D-X—R$^1$ corresponds in each case to a row of Table B.
Table 84
Compounds of the formula (I-I), wherein Q denotes A-84, and D-X—R$^1$ corresponds in each case to a row of Table B.
Table 85
Compounds of the formula (I-0, wherein Q denotes A-85, and D-X—R$^1$ corresponds in each case to a row of Table B.
Table 86
Compounds of the formula (I-I), wherein Q denotes A-86, and D-X—R$^1$ corresponds in each case to a row of Table B.
Table 87
Compounds of the formula (I-I), wherein Q denotes A-87, and D-X—R$^1$ corresponds in each case to a row of Table B.
Table 88
Compounds of the formula (I-I), wherein Q denotes A-88, and D-X—R$^1$ corresponds in each case to a row of Table B.
Table 89
Compounds of the formula (I-I), wherein Q denotes A-89, and D-X—R$^1$ corresponds in each case to a row of Table B.
Table 90
Compounds of the formula (I-I), wherein Q denotes A-90, and D-X—R$^1$ corresponds in each case to a row of Table B.
Table 91
Compounds of the formula (I-I), wherein Q denotes A-91, and D-X—R$^1$ corresponds in each case to a row of Table B.
Table 92
Compounds of the formula (I-I), wherein Q denotes A-92, and D-X—R$^1$ corresponds in each case to a row of Table B.
Table 93
Compounds of the formula (I-I), wherein Q denotes A-93, and D-X—R$^1$ corresponds in each case to a row of Table B.
Table 94
Compounds of the formula (I-I), wherein Q denotes A-94, and D-X—R$^1$ corresponds in each case to a row of Table B.
Table 95
Compounds of the formula (I-II), wherein Q denotes A-95, and D-X—R$^1$ corresponds in each case to a row of Table B.
Table 96
Compounds of the formula (I-I), wherein Q denotes A-96, and D-X—R$^1$ corresponds in each case to a row of Table B.
Table 97
Compounds of the formula (I-I), wherein Q denotes A-97, and D-X—R$^1$ corresponds in each case to a row of Table B.
Table 98
Compounds of the formula (I-I), wherein Q denotes A-98, and D-X—R$^1$ corresponds in each case to a row of Table B.

With respect to their use, further particular preference is given to the compounds (I-II) compiled in the tables below. Moreover, the groups mentioned for a substituent in the tables are on their own, independently of the combination in which they are mentioned, a particularly preferred embodiment of the substituent in question.

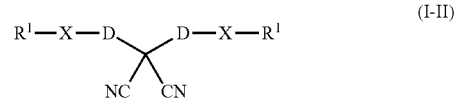
(I-II)

Table 99
Compounds of the formula (I-II) wherein both moieties D-X—R$^1$ are identical and correspond in each case to the same row of Table B.

The compounds of the formula (I) are especially suitable for efficiently combating the following pests:
insects from the order of the lepidopterans (*Lepidoptera*), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Chematobia brumata, Choristoneura furniferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia arnbiguella, Evetria bouliana, Feltia subterranea, Galleria mellonella, Grapholitha funebrana, Grapholitha molesta, Heliothis armigera, Heliothis vire-* scens, Heliothis zea, Hellula undalis, Hibernia defoliaria, Hyphantria cunea, Hyponomeuta malinellus, Keiftria lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis jlammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis, beetles (Coleoptera), for example Agrilus sinuatus, Agriotes lineatus, Agriotes obscurus, Amphimallus solstitialis, Anisandrus dispar, Anthonomus grandis, Anthonomus pomorum, Aphthona euphoridae, A thous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga sp., Phyllopertha horticola, Phyllotreta nemorum, Phyllotreta striolata, Popillia japonica, Sitona lineatus and Sitophilus granaria, flies, mosquitoes (Diptera), e.g. Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops distalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates spp., Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbice, Psila rosae, Psorophora discolor, Prosimulium mixtum, Rhagoletis cerasi, Rhagoletis pomonella, Sarcophaga haemorrhoidalis, Sarcophaga sp., Simulium vittatum, Stomoxys calcitrans, Tabanus bovinus, Tabanus atratus, Tabanus lineola, and Tabanus similis, Tipula oleracea, and Tipula paludosa thrips (Thysanoptera), e.g. Dichromothrips corbetti, Dichromothrips ssp, Frankliniella fusca, Frankliniella occidentalis, Frankliniella tritici, Scirtothrips citri, Thrips oryzae, Thrips palmi and Thrips tabaci, termites (Isoptera), e.g. Calotermes flavicollis, Leucotermes flavipes, Heterotermes aureus, Reticulitermes flavipes, Reticulitermes virginicus, Reticulitermes lucifugus, Termes natalensis, and Coptotertnes formosanus, cockroaches (Blattaria—Blattodea), e.g. Blattella germanica, Blattella asahinae, Periplaneta americana, Periplaneta japonica, Periplaneta brunnea, Periplaneta fulligginosa, Periplaneta australasiae, and Blatta orientalis, true bugs (Hemiptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis potni, Aphis gossypii, Aphis grossulariae, Aphis schneideri, Aphis spiraecola, Aphis sambuci, Acyrthosiphon pisum, Aulacorthum solani, Bernisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma spp., and Arilus critatus ants, bees, wasps, sawflies (Hymenoptera), e.g. Athalia rosae, Atta cephalotes, Atta capiguara, Atta cephalotes, Atta laevigata, Atta robusta, Atta sexdens, Atta texana, Crematogaster spp., Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus spp. Vespula squamosa, Paravespula vulgaris, Paravespula pennsylvanica, Paravespula germanica, Dolichovespula maculata, Vespa crabro, Polistes rubiginosa, Camponotus floridanus, and Linepithema humile, crickets, grasshoppers, locusts (Orthoptera), e.g. Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera, and Locustana pardalina, Arachnoidea, such as arachnids (*Acarina*), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatunz, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei*, and *Eriophyidae* spp. such as *Aculus schlechtendali, Phyllocoptrata oleivora* and *Eriophyes sheldoni*; Tarsonemidae spp. such as *Phytonemus pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and *Tetranychus* urticae, Panonychus ulmi, Panonychus citri, and *Oligonychus pratensis*; Araneida, e.g. *Latrodectus mactans*, and *Loxosceles reclusa*, fleas (*Siphonaptera*), e.g. *Ctenocephalides felis, Ctenocephalides canis, Xenopsylla cheopis, Pulex irritans, Tunga penetrans*, and *Nosopsyllus fasciatus*, silverfish, firebrat (Thysanura), e.g. *Lepisma saccharina* and *Thermobia domestica*, centipedes (Chilopoda), e.g. *Scutigera coleoptrata*, millipedes (Diplopoda), e.g. *Narceus* spp., Earwigs (Dermaptera), e.g. *forficula auricularia*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*, Plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolii*, and other *Heterodera* species; seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenthus* species; ring nematodes, *Criconema* species, *Criconemella* species, *Criconetnoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species; sheath nematodes, *Hemicycliophora* species and *Hemicriconemoides* species; *Hirshmanniella* species; lance nematodes, *Hoplolaimus columbus, Hoplolaimus galeatus* and other *Hoplolaimus* species; false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scribneri, Pratylenchus vulnus, Pratylenchus zeae* and other *Pratylenchus* species; *Radinaphelenchus cocophilus* and other *Radinaphelenchus* species; burrowing nematodes, *Radopholus similis* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species; stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudatum* and other *Xiphinema* species; and other plant parasitic nematode species.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and binders.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates).

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are, e.g., alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are, e.g., mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides can be added to the formulation.

Suitable antifoaming agents are for example antifoaming agents based on silicon or magnesium stearate.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

The compounds of formula (I) can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations: 1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 75 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 75 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

40 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

2. Products to be applied undiluted for foliar applications. For seed treatment purposes, such products may be applied to the seed diluted or undiluted.

H) Dustable Powders (DP, DS)

5 parts by weight of the active compound(s) are ground finely and mixed intimately with 95 parts by weight of finely divided kaolin. This gives a dustable product having 5% (w/w) of active compound(s)

I) Granules (GR, FG, GG, MG)

0.5 part by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

J) ULV Solutions (UL, LS)

10 parts by weight of the active compound(s) are dissolved in 90 parts by weight of an organic solvent, for example xylene. This gives a product having 10% (w/w) of active compound(s), which is applied undiluted for foliar use.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula (I) are effective through both contact (via soil, glass, wall, bed net, carpet, plant parts or animal parts), and ingestion (bait, or plant part) and through trophallaxis and transfer.

According to a preferred embodiment of the invention, the compounds of formula (I) are employed via soil application. Soil application is especially favorable for use against ants, termites, crickets, or cockroaches.

According to another preferred embodiment of the invention, for use against non crop pests such as ants, termites, wasps, flies, mosquitoes, crickets, locusts, or cockroaches the compounds of formula (I) are prepared into a bait preparation.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones. Suitable feeding stimulants are chosen, for example, from animal and/or plant proteins (meat-, fish- or blood meal, insect parts, crickets powder, egg yolk), from fats and oils of animal and/or plant origin, or mono-, oligo- or polyorganosaccharides, especially from sucrose, lactose, fructose, dextrose, glucose, starch, pectin or even molasses or honey, or from salts such as ammonium sulfate, ammonium carbonate or ammonium acetate. Fresh or decaying parts of fruits, crops, plants, animals, insects or specific parts thereof can also serve as a feeding stimulant.

Pheromones are known to be more insect specific. Specific pheromones are described in the literature and are known to those skilled in the art.

The compounds of formula (I) are also suitable for the protection of the seed, plant propagules and the seedlings' roots and shoots, preferably the seeds, against soil pests and also for the treatment plant seeds which tolerate the action of insecticides or fungicides or herbicides owing to breeding, including genetic engineering methods.

Conventional seed treatment formulations include for example flowable concentrates FS, solutions LS, powders for dry treatment DS, water dispersible powders WS or granules for slurry treatment, water soluble powders SS and emulsion ES. Application to the seeds is carried out before sowing directly on the seeds.

The seed treatment application of the compounds of formula (I) or formulations containing them is carried out by spraying or dusting the seeds before sowing of the plants and before emergence of the plants.

The invention also relates to the propagation product of plants, and especially the treated seed comprising, that is, coated with and/or containing, a compound of formula (I) or a composition comprising it. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed comprises the inventive compounds or compositions comprising them in an amount of from 0.1 g to 10 kg per 100 kg of seed.

Compositions of this invention may also contain other active ingredients, for example other pesticides, insecticides, fungicides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list of pesticides together with which the compounds according to the invention can be used, is intended to illustrate the possible combinations, but not to impose any limitation:

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, empenthrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Growth regulators: a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

A.5. Nicotinic receptor agonists/antagonists compounds: clothianidin, dinotefuran, imidacloprid, thiamethoxam, nitenpyram, acetamiprid, thiacloprid;

the thiazol compound of formula (I¹)

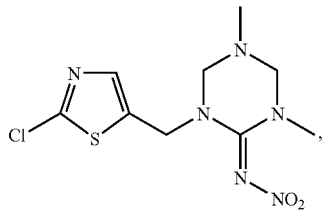

A.6. GABA antagonist compounds: acetoprole, endosulfan, ethiprole, fipronil, vaniliprole, pyrafluprole, pyriprole, the phenylpyrazole compound of formula I²

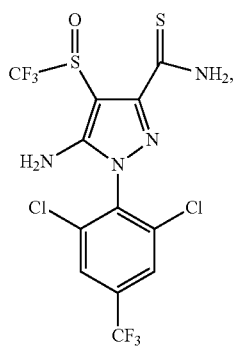

A.7. Macrocyclic lactone insecticides: abamectin, emamectin, milbemectin, lepimectin, spinosad;
A.8. METI I compounds: fenazaquin, pyridaben, tebufenpyrad, tolfenpyrad, flufenerim;
A.9. METI II and III compounds: acequinocyl, fluacyprim, hydramethylnon;
A.10. Uncoupler compounds: chlorfenapyr;
A.11. Oxidative phosphorylation inhibitor compounds: cyhexatin, diafenthiuron, fenbutatin oxide, propargite;
A.12. Moulting disruptor compounds: cyromazine;
A.13. Mixed Function Oxidase inhibitor compounds: piperonyl butoxide;
A.14. Sodium channel blocker compounds: indoxacarb, metaflumizone,
A.15. Various: amitraz, benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula I⁴

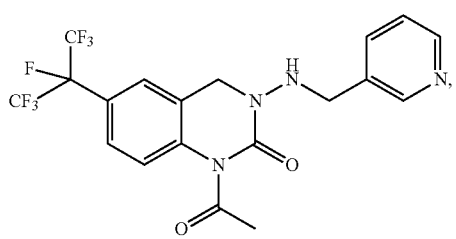

N—R'-2,2-dihalo-1-R'' cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)hydrazone, wherein R' is methyl or ethyl, halo is chloro or bromo, R'' is hydrogen or methyl and R''' is methyl or ethyl, anthranilamide compounds of formula I⁵

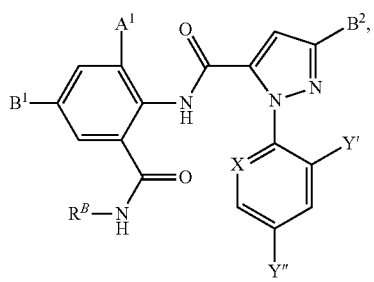

wherein A¹ is CH₃, Cl, Br, I, X is C—H, C—Cl, C—F or N, Y' is F, Cl, or Br, Y'' is H, F, Cl, CF₃, B¹ is hydrogen, Cl, Br, I, CN, B² is Cl, Br, CF₃, OCH₂CF₃, OCF₂H, or OCF₂CHFOCF₃ and R^B is hydrogen, CH₃ or CH(CH₃)₂, and malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds CF₃(CH₂)₂C(CN)₂CH₂(CF₂)₃CF₂H, CF₃(CH₂)₂C(CN)₂CH₂(CF₂)₅CF₂H, CF₃(CH₂)₂C(CN)₂(CH₂)₂C(CF₃)₂F, CF₃(CH₂)₂C(CN)₂(CH₂)₂(CF₂)₃CF₃, CF₂H(CF₂)₃CH₂C(CN)₂CH₂(CF₂)₃CF₂H, CF₃(CH₂)₂C(CN)₂CH₂(CF₂)₃CF₃, CF₃(CF₂)₂CH₂C(CN)₂CH₂(CF₂)₃CF₂H, and CF₃CF₂CH₂C(CN)₂CH₂(CF₂)₃CF₂H.

The commercially available compounds of the group A may be found in The Pesticide Manual, 14th Edition, British Crop Protection Council (2006) among other publications. Thioamides of formula I² and their preparation have been described in WO 98/28279. Lepimectin is known from Agro Project, PJB Publications Ltd, November 2004. Benclothiaz and its preparation have been described in EP-A1454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180. Anthranilamides of formula I⁵ and their preparation have been described in WO 01/70671; WO 02/48137; WO 03/24222, WO 03/15518, WO 04/67528; WO 04/33468; and WO 05/118552. The malononitrile compounds CF₃(CH₂)₂C(CN)₂CH₂(CF₂)₃CF₂H, CF₃(CH₂)₂C(CN)₂CH₂(CF₂)₅CF₂H, CF₃(CH₂)₂C(CN)₂(CH₂)₂C(CF₃)₂F, CF₃(CH₂)₂C(CN)₂(CH₂)₂(CF₂)₃CF₃, CF₂H(CF₂)₃CH₂C(CN)₂CH₂(CF₂)₃CF₂H, CF₃(CH₂)₂C(CN)₂CH₂(CF₂)₃CF₃, CF₃(CF₂)₂CH₂C(CN)₂CH₂(CF₂)₃CF₂H, and CF₃CF₂CH₂C(CN)₂CH₂(CF₂)₃CF₂H have been described in WO 05/63694.

Some of the mixtures of compounds (I) with the above pesticides exhibit a synergistic pesticidal effect.

Preferred are synergistic mixtures comprising a compound of formula (I) and a pesticide selected from the organo(thio)phosphates, carbamates, pyrethroids, growth regulators, neonicotinoids, nicotinic receptor agonists/antagonists compounds, GABA antagonist compounds, macrocyclic lactone insecticides, METI I acaricides, METI II and III compounds, oxidative phosphorylation inhibitor compounds, moulting disruptor compounds, mixed function oxidase inhibitor compound, sodium channel blocker compounds, benclothiaz, bifenazate, cartap, flonicamid, pyridalyl, pymetrozine, sulfur, thiocyclam, N—R'-2,2-dihalo-1-R"cyclo-propanecarboxamide-2-(2,6-dichloro-α,α,α-tri-fluoro-p-tolyphydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, and anthranilamide compounds of formula I'$^3$

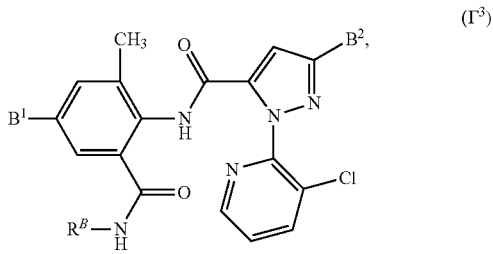

wherein $B^1$ is hydrogen, chlorine or cyano, $B^2$ is a bromine atom or $CF_3$, and $R^B$ is H, $CH_3$ or $CH(CH_3)_2$.

The compounds of formula (I) are useful for controlling pests in all kinds of crops and ornamentals.

They are especifically useful for the seed treatment of such crops.

The compounds of formula (I) are also useful for controlling pests in crops of genetically modified plants. Such plants may show, e.g., tolerance against certain herbicides, or may have insecticidal activity, e.g. by expressing Bt toxins.

In the latter case there may be synergistic effects between the toxin expressed by the plant and the compounds of formula (I).

The compounds of formula (I) are specifically useful for the seed treatment of genetically modified plants.

The pests may be controlled by contacting the target parasite/pest, its food supply, habitat, breeding ground or its locus with a pesticidally effective amount of compounds of or compositions of formula (I).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds or compositions of the invention can also be applied preventively to places at which occurrence of the pests is expected.

The compounds of formula (I) may also be used to protect growing plants from attack or infestation by pests by contacting the plant with a pesticidally effective amount of compounds of formula (I). As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$.

For use in bait compositions, the typical content of active ingredient is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in treating crop plants, the rate of application of the active ingredients of this invention may be in the range of 0.1 g to 4000 g per hectare, desirably from 25 g to 600 g per hectare, more desirably from 50 g to 500 g per hectare.

Compounds of formula (I) and compositions comprising them can also be used for controlling and preventing infestations and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula (I) and compositions comprising them are suitable for systemic and/or non-systemic control of ecto- and/or endoparasites. They are active against all or some stages of development.

Administration can be carried out both prophylactically and therapeutically. Administration of the active compounds is carried out directly or in the form of suitable preparations, orally, topically/dermally or parenterally.

For oral administration to warm-blooded animals, the formula (I) compounds may be formulated as animal feeds, animal feed premixes, animal feed concentrates, pills, solutions, pastes, suspensions, drenches, gels, tablets, boluses and capsules. In addition, the formula (I) compounds may be administered to the animals in their drinking water. For oral administration, the dosage form chosen should provide the animal with 0.01 mg/kg to 100 mg/kg of animal body weight per day of the formula (I) compound, preferably with 0.5 mg/kg to 100 mg/kg of animal body weight per day.

Alternatively, the formula (I) compounds may be administered to animals parenterally, for example, by intraruminal, intramuscular, intravenous or subcutaneous injection. The formula (I) compounds may be dispersed or dissolved in a physiologically acceptable carrier for subcutaneous injection. Alternatively, the formula (I) compounds may be formulated into an implant for subcutaneous administration. In addition the formula (I) compound may be transdermally administered to animals. For parenteral administration, the dosage form chosen should provide the animal with 0.01 mg/kg to 100 mg/kg of animal body weight per day of the formula (I) compound.

The formula (I) compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula (I) compound. In addition, the formula (I) compounds may be formulated as ear tags for animals, particularly quadrupeds such as cattle and sheep.

Suitable preparations are:
  Solutions such as oral solutions, concentrates for oral administration after dilution, solutions for use on the skin or in body cavities, pouring-on formulations, gels;
  Emulsions and suspensions for oral or dermal administration; semi-solid preparations;
  Formulations in which the active compound is processed in an ointment base or in an oil-in-water or water-in-oil emulsion base;
  Solid preparations such as powders, premixes or concentrates, granules, pellets, tablets, boluses, capsules; aerosols and inhalants, and active compound-containing shaped articles.

Generally it is favorable to apply solid formulations which release compounds of formula (I) in total amounts of 10 mg/kg to 300 mg/kg, preferably 20 mg/kg to 200 mg/kg. The active compounds can also be used as a mixture with synergists or with other active compounds which act against pathogenic endo- and ectoparasites.

In general, the compounds of formula (I) are applied in parasiticidally effective amount meaning the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Accordingly, the invention also provides for a process for the preparation of a composition for treating or protecting animals against infestation or infection by parasitical pests which comprises mixing a parasiticidally effective amount of compositions or compounds of formula (I) or their veterinarily acceptable salts, with a veterinarily acceptable carrier.

Further, a veterinary medicament is provided, and the use of the compounds of formula (I) for the manufacture of a veterinary medicament, specifically an antiparasitical veterinary medicament.

In a further aspect of the invention, there is provided the use of compounds of formula (Ia)

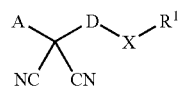

(Ia)

for controlling pests,
wherein
A is D-X—$R^1$ or Q;
X is, independently, oxygen or $S(=O)_n$;
n is 0, 1 or 2;
$R^1$ is, independently, $C_1$-$C_{10}$-alkyl, $C_1$-$C_{10}$-haloalkyl, $C_2$-$C_6$-alkenyl, $C_2$-$C_6$-haloalkenyl, $C_2$-$C_{10}$-alkynyl, $C_3$-$C_{10}$-haloalkynyl, $C_3$-$C_{10}$-cycloalkyl, $C_3$-$C_{10}$-halocycloalkyl, $C_3$-$C_{10}$-cycloalkenyl, $C_3$-$C_{10}$-halocycloalkenyl,
  phenyl or a 5- to 6-membered heteroaromatic ring system which contains 1 to 4 heteroatoms selected from oxygen, nitrogen and sulfur, which heteroaromatic ring is bonded to the X atom via a carbon atom of the ring, and which phenyl or which heteroaromatic ring may be bonded via a $C_1$-$C_{10}$-alkyl group thus forming an aryl-$C_1$-$C_{10}$-alkyl or hetaryl-$C_1$-$C_{10}$-alkyl moiety,
  wherein phenyl or the heteroaromatic ring may be fused to a ring selected from phenyl and a 5- to 6-membered saturated, partially unsaturated or aromatic heterocyclic ring which contains 1 to 3 heteroatoms selected from oxygen, nitrogen and sulfur,
  wherein the hydrogen atoms in the above groups $R^1$ may be partially or in total be replaced by any combination of groups $R^2$;
D is, independently, a saturated or partially unsaturated hydrocarbon chain with one to 5 carbon chain atoms or $C_3$-$C_6$-cycloalkyl, wherein the hydrogen atoms of this chain or of this cycloalkyl may all or in part be replaced with any combination of groups selected from $R^3$;
$R^2$ is halogen, cyano, amino, $C_1$-$C_{10}$-alkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_1$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, tri($C_1$-$C_{10}$)alkylsilyl, or
  phenyl or a 5- to 7-membered saturated or partially unsaturated heterocyclic ring which contains 1 to 3 heteroatoms selected from oxygen, sulfur and nitrogen or a 5- to 6-membered heteroaromatic ring system which contains 1 to 4 heteroatoms selected from oxygen, nitrogen and sulfur, which phenyl or which heterocyclic or heteroaromatic ring may be bonded via an oxygen or a sulfur atom, or
  two groups $R^2$ together with the carbon atom of the hydrocarbon chain may form a 3- to 7-membered saturated or partially unsaturated heterocyclic ring which contains 1 to 3 heteroatoms selected from oxygen, sulfur and nitrogen,
  wherein the above groups $R^2$ are unsubstituted, or the hydrogen atoms in these groups may all or in part be replaced with any combination of groups selected from $R^a$;
$R^3$ is halogen, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_1$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, $C_1$-$C_6$-alkoxycarbonyl, $C_1$-$C_6$-alkenyloxycarbonyl, $C_1$-$C_6$-alkylamino, di($C_1$-$C_6$-alkyl)amino, tri($C_1$-$C_{10}$)alkylsilyl, or
  phenyl or a 5- to 7-membered saturated or partially unsaturated heterocyclic ring which contains 1 to 3 heteroatoms selected from oxygen, sulfur and nitrogen or a 5- to 6-membered heteroaromatic ring system which contains 1 to 4 heteroatoms selected from oxygen, nitrogen and sulfur, which phenyl and which heterocyclic or heteroaromatic ring may be bonded via an oxygen or a sulfur atom,
  wherein the above groups $R^3$ are unsubstituted, or the hydrogen atoms in these groups may all or in part be replaced with any combination of groups selected from $R^a$, or the moiety R³-D-X—R¹ together may form a saturated or unsaturated ring of formula α

(α)

which may have 5 to 7 ring members and besides X 1 to 2 further heteroatoms selected from oxygen, sulfur and nitrogen and which ring may be substituted with 1 to 5 groups selected from $R^a$, or the moiety R³-D-X—R¹ together may form a group of formula β wherein x is 1 to 5

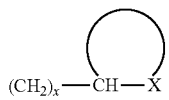

(β)

containing a saturated or unsaturated ring which may have 5 to 7 ring members and besides X 1 to 2 further heteroatoms selected from oxygen, sulfur and nitrogen and which ring may be substituted with 1 to 5 groups selected from $R^a$;

$R^a$ is each independently halogen, cyano, nitro, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, $C_3$-$C_8$-halocycloalkenyl, phenoxy, $OR^i$, $SR^i$, $S(=O)R^i$, $S(=O)_2R^i$, $NR^iR^i$, —$S(=O)_2NR^iR$, $C(=O)R^i$, $C(=O)OR^i$, $C(=O)NR^iR^j$, $C(=NOR^i)R^j$, —$NR^iC(=G)R^j$, —$N[C(=G)R^i]2$, —$NR^iC(=G)OR^j$, —$C(=G)NR^i$—$NR^j_2$, —$NR^iSO_2R^j$, $SiR^i_yR^j_{3-y}$, is 0 to 3), or phenyl or a 5- to 6-membered heteroaromatic ring which contains 1 to 4 heteroatoms selected from oxygen, nitrogen and sulfur, wherein the carbon atoms in phenyl or in the heteroaromatic ring may be substituted with 1 to 5 halogens;

with the proviso that if X is oxygen, then R³ is selected from halogen, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl or tri($C_1$-$C_{10}$)alkylsilyl;

G is oxygen or sulfur;

$R^i$, $R^j$ are each independently hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, or $C_3$-$C_6$-halocycloalkenyl; and Q is $C_1$-$C_{12}$-alkyl, $C_1$-$C_{12}$-haloalkyl, $C_2$-$C_7$-alkenyl, $C_2$-$C_7$-haloalkenyl, $C_2$-$C_7$-alkynyl, $C_2$-$C_7$-haloalkynyl, $C_3$-$C_7$-cycloalkyl, $C_3$-$C_7$-halocycloalkyl, $C_3$-$C_7$-halocycloalkyl-$C_1$-$C_5$-alkyl, wherein each group is unsubstituted or substituted with one or more, preferably 1 to 3, groups $C_3$-$C_7$-cycloalkyl, $C_3$-$C_7$-halocycloalkyl or tri($C_1$-$C_{10}$)alkylsilyl;

and the enantiomers, diastereomers, salts, N-oxides and polymorphs thereof.

The invention is illustrated by the following examples.

I. SYNTHESIS EXAMPLES

The procedures described in the synthesis examples below were used to prepare further compounds I by appropriate modification of the starting compounds. The compounds thus obtained are listed in Table I below, together with physical data.

Example A

Preparation of 2-[(2,2,3,3,4,4,5,5-Octafluoropentyl-2-(trifluoromethylthio)ethyl]-malononitrile (compound I-5)

a) Preparation of 2-(Trifluoromethylthio)ethyl Trifluoromethanesulfonate (I-5a)

To a solution of 2-trifluormethylthioethanol (3.0 g, 20.5 mmol) in anhydrous dichloromethane (30 ml) and N,N-diisopropylethylamine (4.3 ml, 24.6 mmol) at 0° C. was added dropwise trifluoromethanesulfonic anhydride (3.8 ml, 22.6 ml) over 15 min. The reaction mixture was stirred for 2 h at room temperature, quenched with ice-cold water (50 ml), and extracted with dichloromethane (100 ml). The organic layer was washed with 10% citric acid solution (2×75 ml) and brine (2×75 ml), dried ($Na_2SO_4$), filtered, and concentrated under reduced pressure to provide 2-(Trifluoromethylthio)ethyl Trifluoromethanesulfonate (5.0 g, 87%) as a brown liquid: ¹H-NMR (300 MHz, $CDCl_3$) δ=4.66 (t, J=7.2 Hz, 2H), 3.25 (t, J=6.9 Hz, 2H)

b) Preparation of 2,2,3,3,4,4,5,5-Octafluoropentyl Trifluoromethanesulfonate (I-5b)

2,2,3,3,4,4,5,5-Octafluoropentyl Trifluoromethanesulfonate 5b (14.0 g, 89%) was obtained as a brown liquid following the procedure for the preparation of compound 5a using 2,2,3,3,4,4,5,5-Octafluoropentanol (10.0 g, 43.1 mmol), N,N-diisopropylethylamine (9.0 ml, 51.7 mmol) and trifluoromethanesulfonic anhydride (8.0 ml, 47.4 mmol) after stirring overnight:

¹H-NMR (300 MHz, $CDCl_3$) δ=6.06 (tt, J=46.8, 5.1 Hz, 1H), 4.82 (t, J=12.3 Hz, 2H).

c) Preparation of 2-(2,2,3,3,4,4,5,5-Octafluoropentyl)malononitrile (I-5c)

A mixture of compound 5b (15.0 g, 41.2 mmol), malononitrile (5.44 g, 82.4 mmol), and potassium carbonate (28.5 g, 206 mmol) in 1,2-dimethoxymethane (150 ml) was stirred overnight at room temperature under nitrogen. The reaction mixture was quenched with water (150 ml) and extracted with ethyl acetate (2×200 ml). The combined organic extracts were washed with brine (200 ml), dried ($Na_2SO_4$), filtered, and concentrated under reduced pressure. The residue was purified by column chromatography (silica gel, 85:15 hexanes/EtOAc) to provide 2-(2,2,3,3,4,4,5,5-Octafluoropentyl)malononitrile (5c) (7.5 g, 65%) as a white solid:

¹H-NMR (300 MHz, $CDCl_3$) δ=6.06 (tt, J=46.5, 5.1 Hz, 1H), 4.15 (t, J=5.7 Hz, 1H), 2.91 (t, J=16.5 Hz, 2H);

¹⁹F-NMR (282 MHz, $CDCl_3$) δ=−114.2, −125.5, −129.3, −137.4.

d) Preparation of 2-[(2,2,3,3,4,4,5,5-Octafluoropentyl-2-(trifluoromethylthio)ethyl]-malononitrile (compound I-5)

A mixture of 2-(2,2,3,3,4,4,5,5-Octafluoropentyl)malononitrile (5c) (600 mg, 2.14 mmol) and potassium carbonate (600 mg, 4.28 mmol) in 1,2-dimethoxyethane (6 ml) was stirred for 30 min under nitrogen. A solution of 5a (815 mg, 2.91 mmol) in 1,2-dimethoxyethane (2 ml) was added dropwise and the reaction mixture was stirred for 2 h at room temperature. The reaction mixture was quenched with water (50 ml) and extracted with ethyl acetate (2×50 ml). The combined organic layers were washed with brine (50 ml), dried ($Na_2SO_4$), filtered, and concentrated under reduced pressure. The residue was purified by column chromatography (silica gel, 1:1 hexanes/dichloromethane) to provide 2-[(2,2,3,3,4,4,5,5-Octafluoropentyl-2-(trifluoromethylthio)ethyl]-malononitrile (compound I-5) (330 mg, 38%) as an off-white solid having a melting point of 72-74° C.
$^1$H-NMR (300 MHz, $CDCl_3$) δ=6.06 (tt, J=46.5, 5.1 Hz, 1H), 3.27-3.21 (m, 2H), 2.83 (t, J=16.5 Hz, 2H); 2.56-2.50 (m, 2H);
$^{19}$F-NMR (282 MHz, $CDCl_3$) δ=−41.2, −111.7, −125.5, −129.1, −137.3.

Example B

Preparation of 2-[(2,2,3,3,4,4,5,5-Octafluoropentyl-2-(trifluoromethylsulfinyl)ethyl]-malononitrile (compound I-6)

To a solution of 500 mg (1.22 mmol) 2-[(2,2,3,3,4,4,5,5-Octafluoropentyl-2-(trifluoromethylthio)ethyl]-malononitrile (compound I-5) in anhydrous dichloromethane (20 ml) at 0° C. was added m-chloroperbenzoic acid (466 mg, 2.08 mmol, 77% active) and the reaction mixture was stirred for 24 h at room temperature. The reaction mixture was quenched with water (75 ml) and extracted with dichloromethane (2×100 ml). The combined organic extracts were washed with saturated $Na_2S_2O_3$-solution (2×100 ml), and brine (200 ml), dried (Na2SO4), filtered, and concentrated under reduced pressure. The residue was purified by column chromatography (silica gel, 95:5 hexanes/EtOAc) to provide 250 mg (48%) 2-[(2,2,3,3,4,4,5,5-Octafluoropentyl-2-(trifluoromethylsulfinyl)ethyl]-malononitrile (compound I-6) as an off-white solid having a melting point of 107-109° C. $^1$H-NMR (300 MHz, $CDCl_3$) δ=6.06 (tt, J=46.0, 5.1 Hz, 1H), 3.47-3.31 (m, 2H), 2.89 (t, J=16.5 Hz, 2H), 2.80-2.69 (m, 1H), 2.65-2.55 (m, 1H);
$^{19}$F-NMR (282 MHz, $CDCl_3$) δ=−72.5, −111.6, −125.4, −129.0, −137.2.

Example C

Preparation of 2-[(2,2,3,3,4,4,5,5-Octafluoropentyl-2-(trifluoromethylsulfonyl)ethyl]-malononitrile (compound I-15)

Compound I-15 was obtained as a white solid having a melting point of 144-146° C. following the procedure for the preparation of compound I-6 using compound I-5 (410 mg, 1.0 mmol) and m-chloroperbenzoic acid (2.4 g, 11.0 mmol, 77% active) and stirring for 48 h.
$^1$H-NMR (300 MHz, $CDCl_3$) δ=6.07 (tt, J=46.0, 5.1 Hz, 1H), 3.69-3.63 (in, 2H), 2.91 (t, J=16.5 Hz, 2H), 2.74-2.69 (m, 1H);
$^{19}$F-NMR (282 MHz, $CDCl_3$) δ=−77.6, −111.6, −125.4, −128.9, −137.2.

Example D

Preparation of 2-[3-(Trifluoromethylthio)propyl]-2-(2,2,3,3,4,4,5,5,6,6,6-undecafluorohexyl)-malononitrile (compound I-18)

a) Preparation of 2-(Trifluoromethylthio)propyl Trifluoromethanesulfonate (I-18a)

Compound I-18a (390 mg, 72%) was obtained as a brown liquid following the procedure for the preparation of I-5a using 2-trifluormethylthiopropanol (300 mg, 1.87 mmol), N,N-diisopropylethylamine (0.38 ml, 2.2 mmol) and trifluoromethanesulfonic anhydride (0.34 ml, 2.0 mmol).
$^1$H-NMR (300 MHz, $CDCl_3$) δ=4.67 (t, J=6.0 Hz, 2H), 3.03 (t, J=7.2 Hz 2H), 2.30-2.18 (m, 2H);

b) Preparation of 2,2,3,3,4,4,5,5,6,6,6-undecafluorohexyl trifluoromethanesulfonate (I-18b)

2,2,3,3,4,4,5,5,6,6,6-Undecafluorohexyl Trifluoromethanesulfonate (I-18b) (10.8 g, 75%) was obtained as a brown liquid following the procedure for the preparation of compound I-5a using 2,2,3,3,4,4,5,5,6,6,6-Undecafluorohexanol (10.0 g, 33.3 mmol), N,N-diisopropylethylamine (6.9 ml, 40.0 mmol) and trifluoromethanesulfonic anhydride (6.2 ml, 36.6 mmol) after stirring overnight:
$^1$H-NMR (300 MHz, $CDCl_3$) δ=4.82 (t, J=12.3 Hz, 2H).

c) Preparation of 2-(2,2,3,3,4,4,5,5,6,6,6-Undecafluorohexyl)malononitrile (I-18c)

2-(2,2,3,3,4,4,5,5,6,6,6-Undecafluorohexyl)malononitrile (I-18c) (1.63 g, 56%) was obtained as a white solid following the procedure of compound I-5c using I-18b (3.60 g, 8.30 mmol), malononitrile (1.0 g, 16.0 mmol) and potassium carbonate (5.75 g, 41.6 mmol).
$^1$H-NMR (300 MHz, $CDCl_3$) δ=4.14 (t, J=6.9 Hz, 1H), 2.91 (td, J=16.5 Hz, 6.9 Hz 2H);

d) Preparation of 2-[3-(Trifluoromethylthio)propyl]-2-(2,2,3,3,4,4,5,5,6,6,6-undecafluorohexyl)-malononitrile (compound I-18)

135 mg (31%) 2-[3-(trifluoromethylthio)propyl]-2-(2,2,3,3,4',4,5,5,6,6,6-undecafluorohexyl)-malononitrile (compound I-18) were obtained as an off-white solid with a melting point of 88-90° C. following the procedure of compound (compound I-5) using I-18c (300 mg, 0.862 mmol), I-18a (352 mg, 1.20 mmol) and potassium carbonate (238 mg, 1.72 mmol).
$^1$H-NMR (300 MHz, $CDCl_3$) δ=3.05 (t, 0.1=6.6 Hz, 2H), 2.81 (t, J=16.8 Hz, 214), 2.31-2.12 (m, 4H);
$^{19}$F-NMR (282 MHz, $CDCl_3$) δ=−41.2, −81.1, −111.6, −122.7, −123.9, −126.6.

Example E

Preparation of 2-[(2,2,3,3,4,4,5,5-Octafluoropentyl-2-(trifluoromethylthio)ethyl]-malononitrile (compound I-11)

a) Preparation of 2-(2-Chloro-1,1,2-trifluoroethylthio)ethyl Trifluoromethanesulfonate (I-11a)

Compound I-11a (290 mg, 86%) was obtained as a brown liquid following the procedure for the preparation of compound I-5a using 2-(2-chloro-1,1,2-trifluoroethyllthio)ethanol (200 mg, 1.02 mmol) N,N-diisopropylethylamine (0.21 ml, 1.2 mmol) and trifluoromethanesulfonic anhydride (0.19 ml, 1.1 mmol).

$^1$H-NMR (300 MHz, CDCl$_3$) δ=6.23 (dt, J=48.6, 6.5 Hz, 1H), 4.68 (t, J=6.9 Hz 2H), 3.30 (t, J=6.9 Hz 2H).

b) Preparation of 2-[2-(2-chloro-1,1,2-trifluoroethylthio)ethyl]-2-(2,2,3,3,4,4,5,5-Octafluoropentyl)malononitrile (compound I-11)

120 mg (11%) 2-[2-(2-chloro-1,1,2-trifluoroethylthio)ethyl]-2-(2,2,3,3,4,4,5,5-octafluoropentyl)malononitrile (compound I-11) were obtained as an off-white solid with a melting point of 78-80° C. following the procedure of (compound I-5) using I-5c (700 mg, 2.50 mmol), I-11a (1.05 g, 3.24 mmol) and potassium carbonate (630 mg, 5.0 mmol).

$^1$H-NMR (300 MHz, CDCl$_3$) δ=6.30 (dt, J=48.2, 4.5 Hz, 1H), 6.06 (tt, J=46.5, 5.1 Hz, 1H), 3.30-3.23 (m, 2H), 2.83 (t, J=16.5 Hz, 2H), 2.57-2.51 (m, 2H);
$^{19}$F-NMR (282 MHz, CDCl$_3$) δ=−85.4, −111.7, −125.6, −129.1, −137.3, −148.2.

Reference Production Examples

Synthesis of 2-trifluormethylthioethanol

In a 2 l-flask, 100.0 g (1.28 mmol) 2-mercaptoethanol were cooled to −70° C. At this temperature, ammonia was added until 300 ml ammonia had been condensed. At this temperature, 376.1 g (1.92 mol) gaseous trifluormethyliodide was added. UV-Irridiation was started using a mercury vapour lamp (type: Heraeus TQ 150; 150 W). Stirring was continued during the irradiation for 2 h, keeping the temperature at −35° C. The mixture was warmed to ambient temperature overnight.

800 ml diethyl ether and 400 ml 5% NaOH-solution were added. The layers were separated and the aqueous layer was extracted with diethyl ether. The combined organic layers were dried and the solvent was removed (30° C., 450 mbar).

The residue was subjected to a fractionated distillation. The fractions were collected and the first fraction was discarded (boiling point below 65° C.). The product fraction was collected between 65 and 103° C. to yield 168.7 g 2-trifluoromethylthioethanol.

1H-NMR (300 MHz, CDCl$_3$) δ=2.68 (s, 1H), 3.08 (t, 2H), 3.86 (t, 1H);

Synthesis of 2-(2-Chloro-1,1,2-trifluoroethyllthio)ethanol

Under Argon atmosphere, 50.0 g (0.64 mmol) 2-mercaptoethanol were cooled to −10° C. Under stirring 25.6 g (0.64 mmol) of NaH (60% in mineral oil) were added portion wise keeping the internal temperature below −5° C. Stirring was continued for 10 min at −5° C. The reaction vessel was equipped with a dry ice condenser and gaseous chlorotrifluoroethylene was added keeping the internal temperature between 0 and −5° C. Stirring was continued for 10 min at 0° C. and overnight at ambient temperature.

The reaction mixture was poured on ice water and the aqueous layer was extracted three times with methyl tbutyl ether. The combined organic layers were subsequently washed with diluted HCl-solution and brine and dried over MgSO$_4$. The solvent was removed in vacuum and the residue was subjected to a vacuum distillation to yield 15 g 2-(2-Chloro-1,1,2-trifluoroethyllthio)ethanol at 62.6-67.7° C. and 2.05 mbar.

1H-NMR (300 MHz, CDCl$_3$) δ=3.14 (s, 2H), 3.90 (s, 2H), 6.23 (d, 1H);

TABLE I

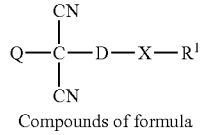

Compounds of formula

| Compound No. | Q | D | X | R$^1$ | Phys. Data |
|---|---|---|---|---|---|
| I-1 | cyclohexyl | —CH$_2$—CH$_2$— | —S— | —CF$_3$ | $^1$H-NMR (300 MHz, CDCl$_3$) δ = 3.17 (m, 2H), 2.33 (m, 2H), 2.03 (m, 2H), 1.93 (m, 2H), 1.78 (m, 2H), 1.33 (m, 5H). |
| I-2 | (CH$_3$)$_3$C— | —CH$_2$—CH$_2$— | —S— | —CF$_3$ | $^1$H-NMR (300 MHz, CDCl$_3$) δ = 3.22 (m, 2H), 2.26 (m, 2H), 1.27 (s, 9H). |
| I-3 | F$_2$C=CH—CH2—CH2— | —CH$_2$—CH$_2$— | —S(O)— | —CF$_3$ | $^1$H-NMR (300 MHz, CDCl$_3$) δ = 4.25 (m, 1H), 3.32 (m, 2H), 2.45 (m, 4H), 2.12 (m, 2H) |
| I-4 | F$_2$C=CF—(CH$_2$)$_2$— | —(CH$_2$)$_2$— | —S(O)— | —CF$_3$ | Mp = 55-57° C. $^1$H-NMR (300 MHz, CDCl$_3$) δ = 3.33 (m, 2H), 2.74 (m, 2H), 2.54 (m, 4H), 2.12 (m, 2H) |
| I-5 | F$_2$HC—(CF$_2$)$_3$—CH$_2$— | —(CH$_2$)$_2$— | —S— | —CF$_3$ | Mp = 72-74° C. $^1$H-NMR (300 MHz, CDCl$_3$) δ = 6.06 (tt, J = 46.5, 5.1 Hz, 1H), 3.27-3.21 (m, 2H),. 2.83 (t, J = 16.5 Hz, 2H); 2.56-2.50 (m, 2H); $^{19}$F-NMR (282 MHz, CDCl$_3$) δ = 41.2, −111.7, −125.5, −129.1, −137.3.) |
| I-6 | F$_2$HC—(CF$_2$)$_3$—CH$_2$— | —(CH$_2$)$_2$— | —S(O)— | —CF$_3$ | Mp = 107-109° C. $^1$H-NMR (300 MHz, CDCl$_3$) δ = 6.06 (tt, J = 46.0, 5.1 Hz, 1H), 3.47-3.31 (m, 2H),. 2.89 (t, J = 16.5 Hz, 2H), 2.80-2.69 (m, 1H), 2.65-2.55 (m, 1H); $^{19}$F-NMR (282 MHz, CDCl$_3$) δ = −72.5, −111.6, −125.4, −129.0, −137.2.) |

TABLE I-continued $$Q-\underset{\underset{CN}{|}}{\overset{\overset{CN}{|}}{C}}-D-X-R^1$$

Compounds of formula

| Compound No. | Q | D | X | $R^1$ | Phys. Data |
|---|---|---|---|---|---|
| I-7 | $F_2HC-(CF_2)_5-CH_2-$ | $-(CH_2)_2-$ | $-S-$ | $-CF_3$ | Mp = 103.00-105.00<br>$^1$H-NMR (300 MHz, CDCl$_3$) δ = 6.06 (tt, J = 47.0, 5.0 Hz, 1H), 3.11-3.03 (m, 2H), 2.81 (t, J = 16.5 Hz, 2H), 2.30-2.16 (m, 1H);<br>$^{19}$F-NMR (282 MHz, CDCl$_3$) δ = −41.3, −111.5, −122.0, −123.8, −129.6, −137.4. |
| I-8 | $F_3C-(CF_2)_4-CH_2-$ | $-(CH_2)_2-$ | $-S-$ | $-CF_3$ | $^1$H-NMR (300 MHz, CDCl$_3$) δ = 3.27-3.21 (m, 2H), 2.82 (t, J = 16.5 Hz, 2H), 2.55-2.50 (m, 2H);<br>$^{19}$F-NMR (282 MHz, CDCl$_3$) δ = −41.2, −81.1, −111.6, −122.7, −123.9, −126.6 |
| I-9 | $F_3C-(CF_2)_4-CH_2-$ | $-(CH_2)_2-$ | $-S-$ | $-CF_2-CHFCL$ | Mp = 122.00-124.00<br>$^1$H-NMR (300 MHz, CDCl$_3$) δ = 6.23 (dt, J = 48.6, 5.5 Hz, 1H), 3.29-3.23 (m, 2H), 2.82 (t, J = 16.5 Hz, 2H), 2.56-2.50 (m, 2H);;<br>$^{19}$F-NMR (282 MHz, CDCl$_3$) δ = −85.4, −111.5, −122.7, −123.9, −126.6, −148.4. |
| I-10 | $F_2HC-(CF_2)_5-CH_2-$ | $-(CH_2)_2-$ | $-S(O)-$ | $-CF_3$ | Mp = 123.00-125.00<br>$^1$H-NMR (300 MHz, CDCl$_3$) δ = 6.06 (tt, J = 46.8, 5.0 Hz, 1H), 3.43-3.36 (m, 2H), 2.90 (t, J = 16.3 Hz, 2H), 2.70-2.53 (m, 1H), 2.79-2.72 (m, 1H);<br>$^{19}$F-NMR (282 MHz, CDCl$_3$) δ = −72.5, −111.4, −122.0, −123.7, −129.5, −137.3. |
| I-11 | $F_2HC-(CF_2)_3-CH_2-$ | $-(CH_2)_2-$ | $-S-$ | $-CF_2-CHFCL$ | Mp = 78.00-80.00;<br>$^1$H-NMR (300 MHz, CDCl$_3$) δ = 6.30 (dt, J = 48.2, 4.5 Hz, 1H), 6.06 (tt, J = 46.5, 5.1 Hz, 1H), 3.30-3.23 (m, 2H), 2.83 (t, J = 16.5 Hz, 2H), 2.57-2.51 (m, 2H);<br>$^{19}$F-NMR (282 MHz, CDCl$_3$) δ = −85.4, −111.7, −125.6, −129.1, −137.3, −148.2. |
| I-12 | $F_3C-(CF_2)_4-CH_2-$ | $-(CH_2)_2-$ | $-S(O)-$ | $-CF_3$ | Mp = 160.00-162.00;<br>$^1$H-NMR (300 MHz, CDCl$_3$) δ = 3.49-3.36 (m, 2H), 2.89 (t, J = 16.5 Hz, 2H), 2.81-2.52 (m, 2H);<br>$^{19}$F-NMR (282 MHz, CDCl$_3$) δ = −72.5, −81.1, −111.4, −122.7, −123.7, −126.1. |
| I-13 | $F_2HC-(CF_5)_5-CH_2-$ | $-(CH_2)_2-$ | $-S(O)_2-$ | $-CF_3$ | Mp = 145.00-147.00<br>$^1$H-NMR (300 MHz, CDCl$_3$) δ = 6.06 (tt, J = 47.0, 5.0 Hz, 1H), 3.69-3.63 (m, 2H), 2.91 (t, J = 16.5 Hz, 2H), 2.85-2.68 (m, 2H);<br>$^{19}$F-NMR (282 MHz, CDCl$_3$) δ = −77.6, −111.3, −121.9, −123.6, −129.5, −137.3. |
| I-14 | $F_3C-(CF_2)_4-CH_2-$ | $-(CH_2)_2-$ | $-S(O)_2-$ | $-CF_3$ | Mp = 146.00-148.00<br>$^1$H-NMR (300 MHz, CDCl$_3$ + 2 drops of acetone-d$_6$) δ = 3.69-3.64 (m, 2H), 2.93 (t, J = 16.5 Hz, 2H), 2.74-2.69 (m, 2H);<br>$^{19}$F-NMR (282 MHz, CDCl$_3$ +2 drops of acetone-d$_6$) δ = −77.6, −81.0, −111.4, −122.7, −123.7, −126.5. |
| I-15 | $F_2HC-(CF_2)_3-CH_2-$ | $-(CH_2)_2-$ | $-S(O)_2-$ | $-CF_3$ | Mp = 144-146° C.<br>$^1$H-NMR (300 MHz, CDCl$_3$) δ = 6.07 (tt, J = 46.0, 5.1 Hz, 1H), 3.69-3.63 (m, 2H), 2.91 (t, J = 16.5 Hz, 2H), 2.80-2.69 (m, 1H), 2.74-2.69 (m, 2H).<br>$^{19}$F-NMR (282 MHz, CDCl$_3$) δ = −77.6, −111.6, −125.4, −128.9, −137.2. |
| I-16 | $F_2HC-(CF_2)_5-CH_2-$ | $-(CH_2)_2-$ | $-S-$ | $-CF_2-CHFCL$ | Mp = 112.00-114.00<br>$^1$H-NMR (300 MHz, CDCl$_3$) δ = 6.23 (dt, J = 48.6, 5.5 Hz, 1H), 6.06 (tt, J = 47.0, 5.0 Hz, 1H), 3.29-3.23 (m, 2H), 2.84 (t, J = 16.5 Hz, 2H), 2.56-2.50 (m, 2H).<br>$^{19}$F-NMR (282 MHz, CDCl$_3$) δ = −85.4, −111.6, −122.0, −123.7, −129.6, −137.4, −148.3. |
| I-17 | $F_2HC-(CF_2)_5-CH_2-$ | $-(CH_2)_3-$ | $-S-$ | $-CF_3$ | Mp = 87.00-89.00<br>$^1$H-NMR (300 MHz, CDCl$_3$) δ = 6.06 (tt, J = 46.8, 5.0 Hz, 1H), 3.07-3.03 (m, 2H), 2.81 (t, J = 16.5 Hz, 2H), 2.30-2.16 (m, 4H).<br>$^{19}$F-NMR (282 MHz, CDCl$_3$) δ = −41.2, −111.7, −122.0, −123.8, −129.7, −137.4. |
| I-18 | $F_3C-(CF_2)_4-CH_2-$ | $-(CH_2)_3-$ | $-S-$ | $-CF_3$ | Mp = 88.00-90.00<br>$^1$H-NMR (300 MHz, CDCl$_3$) δ = 3.05 (t, J = 6.6 Hz, 2H), 2.81 (t, J = 16.8 Hz, 2H), 2.31-2.12 (m, 4H).<br>$^{19}$F-NMR (282 MHz, CDCl$_3$) δ = −41.2, −81.1, −111.6, −122.7, −123.9, −126.6. |

TABLE I-continued

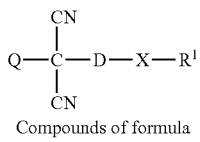

Compounds of formula

| Compound No. | Q | D | X | R¹ | Phys. Data |
|---|---|---|---|---|---|
| I-19 | $F_2HC-(CF_2)_3-CH_2-$ | $-(CH_2)_3-$ | $-S-$ | $-CF_3$ | Mp = 54.00-56.00<br>$^1$H-NMR (300 MHz, CDCl$_3$) δ = 6.07 (tt, J = 46.5, 5.1 Hz, 1H), 3.05 (t, J = 6.5 Hz, 2H), 2.81 (t, J = 16.7 Hz, 2H), 2.30-2.16 (m, 4H).<br>$^{19}$F-NMR (282 MHz, CDCl$_3$) δ = -41.2, -111.8, -125.6, -129.2, -137.3. |

II. USE

Examples for the Action Against Harmful Pests

1. Activity against Boll Weevil (*Anthonomus grandis*)

The active compounds are formulated in 1:3 DMSO:water. 10 to 15 eggs placed into microtiterplates filled with 2% agar-agar in water and 300 ppm formaline. The eggs are sprayed with 20 µl of the test solution, the plates are sealed with pierced foils and kept at 24-26° C. and 75-85% humidity with a day/night cycle for 3 to 5 days. Mortality is assessed on the basis of the remaining unhatched eggs or larvae on the agar surface and/or quantity and depth of the digging channels caused by the hatched larvae. Tests are replicated 2 times.

In this test the compounds I-3, I-4, I-5, I-6, I-7, I-8, I-10, I-12, I-13, I-15, and I-19 showed an activity of more than 90%.

2. Activity against Mediterranean Fruit Fly (*Ceratitis capitata*)

The active compounds are formulated in 1:3 DMSO:water. 50 to 80 eggs are placed into microtiterplates filled with 0.5% agar-agar and 14% diet in water. The eggs are sprayed with 5 µl of the test solution, the plates are sealed with pierced foils and kept at 27-29° C. and 75-85% humidity under fluorescent light for 6 days. Mortality is assessed on the basis of the agility of the hatched larvae. Tests are replicated 2 times.

In this test the compounds I-5, I-6, I-7, I-8, I-11, I-12, I-15, and I-19 showed an activity of more than 90%.

3. Activity against Tobacco Budworm (*Heliothis virescens*)

The active compounds are formulated in 1:3 DMSO:water. 15 to 25 eggs are placed into microtiterplates filled with diet. The eggs are sprayed with 10 µl of the test solution, the plates are sealed with pierced foils and kept at 27-29° C. and 75-85% humidity under fluorescent light for 6 days. Mortality is assessed on the basis of the agility and of comparative feeding of the hatched larvae. Tests are replicated 2 times.

4. Activity against Vetch Aphid (*Megoura viciae*)

The active compounds are formulated in 1:3 DMSO:water. Bean leaf disks are placed into microtiterplates filled with 0.8% agar-agar and 2.5 ppm OPUS™. The leaf disks are sprayed with 2.5 µl of the test solution and 5 to 8 adult aphids are placed into the microtiterplates which are then closed and kept at 22-24° C. and 35-45% under fluorescent light for 6 days. Mortality is assessed on the basis of vital, reproduced aphids. Tests are replicated 2 times.

5. Activity against Wheat Aphid (*Rhopalosiphum padi*)

The active compounds are formulated in 1:3 DMSO:water. Barley leaf disks are placed into microtiterplates filled with 0.8% agar-agar and 2.5 ppm OPUS™. The leaf disks are sprayed with 2.5 µl of the test solution and 3 to 8 adult aphids are placed into the microtiterplates which are then closed and kept at 22-24° C. and 35-45% humidity under fluorescent light for 5 days. Mortality is assessed on the basis of vital aphids. Tests are replicated 2 times.

6. Activity against Cotton Aphid (*Aphis gossypii*)

The active compounds are formulated in 50:50 acetone: water and 100 ppm Kinetic™ surfactant.

Cotton plants at the cotyledon stage (one plant per pot) are infested by placing a heavily infested leaf from the main colony on top of each cotyledon. The aphids are allowed to transfer to the host plant overnight, and the leaf used to transfer the aphids is removed. The cotyledons are dipped in the test solution and allowed to dry. After 5 days, mortality counts are made.

7. Activity against Southern Armyworm (*Spodoptera eridania*), 2nd Instar Larvae The active compounds are formulated for testing the activity against insects and arachnids as a 10.000 ppm solution in a mixture of 35% acetone and water, which is diluted with water, if needed.

A Sieva lima bean leaf is dipped in the test solution and allowed to dry. The leaf is then placed in a petri dish containing a filter paper on the bottom and ten 2nd instar caterpillars. At 5 days, observations are made of mortality and reduced feeding.

8. Activity against Argentine ant (*Linepithema humile*), harvester ant (*Pogonomyrmex californicus*), acrobat ant (*Crematogaster* spp.), carpenter ant (*Camponotus floridanus*), fire ant (*Solenopsis invicta*), house fly (*Musca domestica*), stable fly (*Stomoxys calcitrans*), flesh fly (*Sarcophaga* sp.), yellowfever mosquito (*Aedes aegyptii*), house mosquito (*Culex quinquefasciatus*), malaria mosquito (*Anopheles albinzanus*), German cockroach (*Blattella Germanica*), cat flea (*Ctenocephalides felis*), and brown dog tick (*Rhipicephalus sanguineus*) via glass contact Glass vials are treated with 0.5 ml of a solution of active ingredient in acetone and allowed to dry. Insects or ticks are placed into each vial together with some food and moisture supply. The vials are kept at 22° C. and are observed for treatment effects at various time intervals.

9. Activity against yellowfever mosquito (*Aedes aegyptii*), house mosquito (*Culex quinquefasciatus*) and malaria mosquito (*Anopheles albimanus*) larvae via water treatment Well plates are used as test arenas. The active ingredient is dissolved in acetone and diluted with water to obtain the concentrations needed. The diluted solutions containing appr. 1% acetone are placed into each well. Approximately 10 mosquito larvae ($4^{th}$-instars) in 1 ml water are added to each well. Larvae are fed one drop of liver powder each day. The dishes are covered and maintained at 22° C. Mortality is recorded daily and dead larvae and live or dead pupae are removed daily. At the end of the test remaining live larvae are recorded and percent mortality is calculated.

The invention claimed is:
1. A method of protecting growing plants from attack or infestation by pests by applying to the plants, or to the soil or water in which they are growing, a pesticidally effective amount of a compound of formula (I),

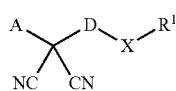

wherein
A is D-X—$R^1$ or Q;
X is, independently, oxygen or $S(=O)_n$;
n is 0, 1 or 2;
$R^1$ is, independently, $C_1$-$C_{10}$-alkyl, $C_1$-$C_{10}$-haloalkyl, $C_2$-$C_6$-alkenyl, $C_2$-$C_6$-haloalkenyl, $C_2$-$C_{10}$-alkynyl, $C_3$-$C_{10}$-haloalkynyl, $C_3$-$C_{10}$-cycloalkyl, $C_3$-$C_{10}$-halocycloalkyl, $C_3$-$C_{10}$-cycloalkenyl or $C_3$-$C_{10}$-halocycloalkenyl,
phenyl or a 5- to 6-membered heteroaromatic ring system which contains 1 to 4 heteroatoms selected from the group consisting of oxygen, nitrogen and sulfur, which heteroaromatic ring is bonded to the X atom via a carbon atom of the ring, and which phenyl or which heteroaromatic ring may be bonded via a $C_1$-$C_{10}$-alkyl group thus forming an aryl-$C_1$-$C_{10}$-alkyl or hetaryl-$C_1$-$C_{10}$-alkyl moiety,
wherein phenyl or the heteroaromatic ring may be fused to a ring selected from phenyl and a 5- to 6-membered saturated, partially unsaturated or aromatic heterocyclic ring which contains 1 to 3 heteroatoms selected from the group consisting of oxygen, nitrogen and sulfur,
wherein the hydrogen atoms in the above groups $R^1$ may be partially or in total be replaced by any combination of groups $R^2$;
D is, independently, a saturated or partially unsaturated hydrocarbon chain with one to 5 carbon chain atoms or $C_3$-$C_6$-cycloalkyl, wherein the hydrogen atoms of this chain or of this cycloalkyl may all or in part be replaced with any combination of groups selected from $R^3$;
$R^2$ is halogen, cyano, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, tri($C_1$-$C_{10}$)alkylsilyl, or
phenyl or a 5- to 7-membered saturated or partially unsaturated heterocyclic ring which contains 1 to 3 heteroatoms selected from the group consisting of oxygen, sulfur and nitrogen or a 5- to 6-membered heteroaromatic ring system which contains 1 to 4 heteroatoms selected from the group consisting of oxygen, nitrogen and sulfur, which phenyl or which heterocyclic or heteroaromatic ring may be bonded via an oxygen or a sulfur atom, or
two groups $R^2$ together with the carbon atom of the hydrocarbon chain may form a 3- to 7-membered saturated or partially unsaturated heterocyclic ring which contains 1 to 3 heteroatoms selected from the group consisting of oxygen, sulfur and nitrogen,
wherein the above groups $R^2$ are unsubstituted, or the hydrogen atoms in these groups may all or in part be replaced with any combination of groups selected from $R^a$;
$R^3$ is halogen, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, $C_1$-$C_6$-alkoxycarbonyl, $C_1$-$C_6$-alkenyloxycarbonyl, $C_1$-$C_6$-alkylamino, di($C_1$-$C_6$-alkyl)amino, tri($C_1$-$C_{10}$)alkylsilyl, or
phenyl or a 5- to 7-membered saturated or partially unsaturated heterocyclic ring which contains 1 to 3 heteroatoms selected from the group consisting of oxygen, sulfur and nitrogen or a 5- to 6-membered heteroaromatic ring system which contains 1 to 4 heteroatoms selected from the group consisting of oxygen, nitrogen and sulfur, which phenyl and which heterocyclic or heteroaromatic ring may be bonded via an oxygen or a sulfur atom,
wherein the above groups $R^3$ are unsubstituted, or the hydrogen atoms in these groups may all or in part be replaced with any combination of groups selected from $R^a$, or
the moiety $R^3$-D-X—$R^1$ together may form a saturated or unsaturated ring of formula α

which may have 5 to 7 ring members and besides X, 1 to 2 further heteroatoms selected from the group consisting of oxygen, sulfur and nitrogen and which ring may be substituted with 1 to 5 groups selected from $R^a$,
$R^a$ is each independently halogen, cyano, nitro, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, $C_3$-$C_8$-halocycloalkenyl, phenoxy, $OR^i$, $SR^i$, $S(=O)R^i$, $S(=O)_2R^i$, $NR^iR^j$, —$S(=O)_2NR^iR$, $C(=O)R^i$, $C(=O)OR^i$, $C(=O)NR^iR^j$, $C(=NOR^i)R^j$, —$NR^iC(=G)R^j$, —$N[C(=G)R^i]2$, —$NR^iC(=G)OR^j$, —$C(=G)NR^i$—$NR^j_2$, —$NR^iSO_2R^j$, $SiR^i_yR^j_{3-y}$ (y is 0 to 3), or
phenyl or a 5- to 6-membered heteroaromatic ring which contains 1 to 4 heteroatoms selected from the group consisting of oxygen, nitrogen and sulfur, wherein the carbon atoms in phenyl or in the heteroaromatic ring may be substituted with 1 to 5 halogens;
with the proviso that if X is oxygen, then $R^3$ is selected from the group consisting of halogen, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl and tri($C_1$-$C_{10}$)alkylsilyl;

G is oxygen or sulfur;

$R^i$, $R^j$ are each independently hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkenyl, or $C_3$-$C_6$-halocycloalkenyl; and Q is $C_1$-$C_{12}$-alkyl, $C_1$-$C_{12}$-haloalkyl, $C_2$-$C_7$-alkenyl, $C_2$-$C_7$-haloalkenyl, $C_2$-$C_7$-alkynyl, $C_2$-$C_7$-haloalkynyl, $C_3$-$C_7$-cycloalkyl, $C_3$-$C_7$-halocycloalkyl, $C_3$-$C_7$-cycloalkyl-$C_1$-$C_5$-alkyl, or $C_3$-$C_7$-halocycloalkyl-$C_1$-$C_5$-alkyl, wherein each group is unsubstituted or substituted with one or more, groups $C_3$-$C_7$-cycloalkyl, $C_3$-$C_7$-halocycloalkyl or tri($C_1$-$C_{10}$)alkylsilyl;

and the enantiomers, diastereomers, salts, and N-oxides thereof.

2. The method of claim 1 wherein A in formula (I) is Q.

3. The method of claim 1 wherein A in formula (I) is D-X—$R^1$.

4. The method of claim 1,
wherein in formula (I)
A is Q;
X is S(=O)$_n$;
n is 0, 1 or 2;
$R^1$ is $C_1$-$C_{10}$-alkyl or $C_1$-$C_{10}$-haloalkyl;
D is a saturated hydrocarbon chain with one to 5 carbon chain atoms; and
Q is $C_1$-$C_{12}$-alkyl or $C_1$-$C_{12}$-haloalkyl.

5. The method of claim 1,
wherein in formula (I)
A is Q;
X is S(=O)$_n$;
n is 0, 1 or 2;
$R^1$ is $C_1$-$C_6$-haloalkyl;
D is a saturated hydrocarbon chain with one to 3 carbon chain atoms; and
Q is $C_1$-$C_{12}$-fluoroalkyl.

6. A process for the preparation of a compound of formula (I)

(I)

wherein
A is D-X—$R^1$ or Q;
X is, independently, oxygen or S(=O)$_n$;
n is 0, 1 or 2;
$R^1$ is, independently, $C_1$-$C_{10}$-alkyl, $C_1$-$C_{10}$-haloalkyl, $C_2$-$C_6$-alkenyl, $C_2$-$C_6$-haloalkenyl, $C_2$-$C_{10}$-alkynyl, $C_3$-$C_{10}$-haloalkynyl, $C_3$-$C_{10}$-cycloalkyl, $C_3$-$C_{10}$-halocycloalkyl, $C_3$-$C_{10}$-cycloalkenyl or $C_3$-$C_{10}$-halocycloalkenyl, phenyl or a 5- to 6-membered heteroaromatic ring system which contains 1 to 4 heteroatoms selected from the group consisting of oxygen, nitrogen and sulfur, which heteroaromatic ring is bonded to the X atom via a carbon atom of the ring, and which phenyl or which heteroaromatic ring may be bonded via a $C_1$-$C_{10}$-alkyl group thus forming an aryl-$C_1$-$C_{10}$-alkyl or hetaryl-$C_1$-$C_{10}$-alkyl moiety, wherein phenyl or the heteroaromatic ring may be fused to a ring selected from phenyl and a 5- to 6-membered saturated, partially unsaturated or aromatic heterocyclic ring which contains 1 to 3 heteroatoms selected from the group consisting of oxygen, nitrogen and sulfur, wherein the hydrogen atoms in the above groups $R^1$ may be partially or in total be replaced by any combination of groups $R^2$;

D is, independently, a saturated or partially unsaturated hydrocarbon chain with one to 5 carbon chain atoms or $C_3$-$C_6$-cycloalkyl, wherein the hydrogen atoms of this chain or of this cycloalkyl may all or in part be replaced with any combination of groups selected from $R^3$;

$R^2$ is halogen, cyano, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, tri($C_1$-$C_{10}$)alkylsilyl, or phenyl or a 5- to 7-membered saturated or partially unsaturated heterocyclic ring which contains 1 to 3 heteroatoms selected from the group consisting of oxygen, sulfur and nitrogen or a 5- to 6-membered heteroaromatic ring system which contains 1 to 4 heteroatoms selected from the group consisting of oxygen, nitrogen and sulfur, which phenyl or which heterocyclic or heteroaromatic ring may be bonded via an oxygen or a sulfur atom, or two groups $R^2$ together with the carbon atom of the hydrocarbon chain may form a 3- to 7-membered saturated or partially unsaturated heterocyclic ring which contains 1 to 3 heteroatoms selected from the group consisting of oxygen, sulfur and nitrogen, wherein the above groups $R^2$ are unsubstituted, or the hydrogen atoms in these groups may all or in part be replaced with any combination of groups selected from $R^a$;

$R^3$ is halogen, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, $C_1$-$C_6$-alkoxycarbonyl, $C_1$-$C_6$-alkenyloxycarbonyl, $C_1$-$C_6$-alkylamino, di($C_1$-$C_6$-alkyl)amino, tri($C_1$-$C_{10}$)alkylsilyl, or phenyl or a 5- to 7-membered saturated or partially unsaturated heterocyclic ring which contains 1 to 3 heteroatoms selected from the group consisting of oxygen, sulfur and nitrogen or a 5- to 6-membered heteroaromatic ring system which contains 1 to 4 heteroatoms selected from the group consisting of oxygen, nitrogen and sulfur, which phenyl and which heterocyclic or heteroaromatic ring may be bonded via an oxygen or a sulfur atom, wherein the above groups $R^3$ are unsubstituted, or the hydrogen atoms in these groups may all or in part be replaced with any combination of groups selected from $R^a$, or the moiety $R^3$-D-X—$R^1$ together may form a saturated or unsaturated ring of formula α

(α)

which may have 5 to 7 ring members and besides X, 1 to 2 further heteroatoms selected from the group consisting of oxygen, sulfur and nitrogen and which ring may be substituted with 1 to 5 groups selected from $R^a$, $R^a$ is each independently halogen, cyano, nitro, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, $C_3$-$C_8$-halocycloalkenyl, phenoxy, $OR^i$, $SR^i$, $S(=O)R^i$, $S(=O)_2R^i$, $NR^iR^j$, —$S(=O)_2NR$, $C(=O)R^i$, $C(=O)OR^i$, $C(=O)NR^iR^j$, $C(=NOR^i)R^j$, —$NR^iC(=G)R^j$, —$N[C(=G)R^i]2$, —$NR^iC(=G)OR^j$, —$C(=G)NR^i$—$NR^j_2$, —$NR^iSO_2R^j$, $SiR^i_y R^j_{3-y}$ (y is 0 to 3), or phenyl or a 5- to 6-membered heteroaromatic ring which contains 1 to 4 heteroatoms selected from the group consisting of oxygen, nitrogen and sulfur, wherein the carbon atoms in phenyl or in the heteroaromatic ring may be substituted with 1 to 5 halogens;

with the proviso that if X is oxygen, then $R^3$ is selected from the group consisting of halogen, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl and tri($C_1$-$C_{10}$)alkylsilyl;

G is oxygen or sulfur;

$R^i$, $R^j$ are each independently hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, or $C_3$-$C_6$-halocycloalkenyl; and Q is $C_1$-$C_{12}$-alkyl, $C_1$-$C_{12}$-haloalkyl, $C_2$-$C_7$-alkenyl, $C_2$-$C_7$-haloalkenyl, $C_2$-$C_7$-alkynyl, $C_2$-$C_7$-haloalkynyl, $C_3$-$C_7$-cycloalkyl, $C_3$-$C_7$-halocycloalkyl, $C_3$-$C_7$-cycloalkyl-$C_1$-$C_5$-alkyl, or $C_3$-$C_7$-halocycloalkyl-$C_1$-$C_8$-alkyl, wherein each group is unsubstituted or substituted with one or more, groups $C_3$-$C_7$-cycloalkyl, $C_3$-$C_7$-halocycloalkyl or tri($C_1$-$C_{10}$)alkylsilyl;

which comprises reacting a compound (II) with a compound (III) in the presence of a base to give compound (I),

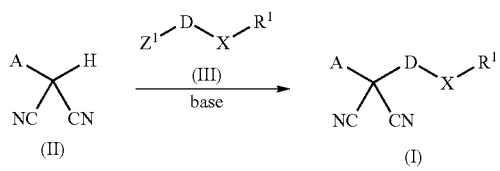

wherein $Z^1$ represents a suitable leaving group.

7. The process of claim 6, wherein two equivalents of a compound (III) are reacted with malononitrile in the presence of a base:

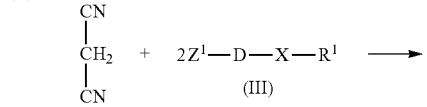

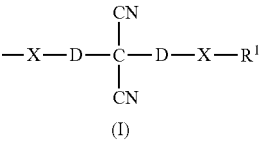

wherein D, X, $R^1$ are defined as in claim 5 and $Z^1$ is a suitable leaving group.

8. A compound of formula (I),

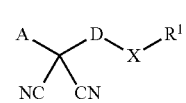

wherein

A is D-X—$R^1$ or Q;

n is 0, 1 or 2;

$R^1$ is, independently, $C_1$-$C_{10}$-alkyl, $C_1$-$C_{10}$-haloalkyl, $C_2$-$C_6$-alkenyl, $C_2$-$C_6$-haloalkenyl, $C_2$-$C_{10}$-alkynyl, $C_3$-$C_{10}$-haloalkynyl, $C_3$-$C_{10}$-cycloalkyl, $C_3$-$C_{10}$-halocycloalkyl, $C_3$-$C_{10}$-cycloalkenyl or $C_3$-$C_{10}$-halocycloalkenyl, phenyl or a 5- to 6-membered heteroaromatic ring system which contains 1 to 4 heteroatoms selected from the group consisting of oxygen, nitrogen and sulfur, which heteroaromatic ring is bonded to the X atom via a carbon atom of the ring, and which phenyl or which heteroaromatic ring may be bonded via a $C_1$-$C_{10}$-alkyl group thus forming an aryl-$C_1$-$C_{10}$-alkyl or hetaryl-$C_1$-$C_{10}$-alkyl moiety, wherein phenyl or the heteroaromatic ring may be fused to a ring selected from phenyl and a 5- to 6-membered saturated, partially unsaturated or aromatic heterocyclic ring which contains 1 to 3 heteroatoms selected from the group consisting of oxygen, nitrogen and sulfur, wherein the hydrogen atoms in the above groups $R^1$ may be partially or in total be replaced by any combination of groups $R^2$;

D is, independently, a saturated or partially unsaturated hydrocarbon chain with one to 5 carbon chain atoms or $C_3$-$C_6$-cycloalkyl, wherein the hydrogen atoms of this chain or of this cycloalkyl may all or in part be replaced with any combination of groups selected from $R^3$;

$R^2$ is halogen, cyano, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, tri ($C_1$-$C_{10}$)alkylsilyl, or phenyl or a 5- to 7-membered saturated or partially unsaturated heterocyclic ring which contains 1 to 3 heteroatoms selected from the group consisting of oxygen, sulfur and nitrogen or a 5- to 6-membered heteroaromatic ring system which contains 1 to 4 heteroatoms selected from the group consisting of oxygen, nitrogen and sulfur, which phenyl or which heterocyclic or heteroaromatic ring may be bonded via an oxygen or a sulfur atom, or two groups $R^2$ together with the carbon atom of the hydrocarbon chain may form a 3- to 7-membered saturated or partially unsaturated heterocyclic ring which contains 1 to 3 heteroatoms selected from the group consisting of oxygen, sulfur and nitrogen, wherein the above groups $R^2$ are unsubstituted, or the hydrogen atoms in these groups may all or in part be replaced with any combination of groups selected from $R^a$;

$R^3$ is halogen, amino, $C_1$-$C_{10}$-alkyl, $C_1$-$C_{10}$-haloalkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_1$-$C_6$-alkoxy, $C_2$-$C_6$-alkenyloxy, $C_3$-$C_6$-alkynyloxy, $C_1$-$C_6$-haloalkoxy, $C_2$-$C_6$-haloalkenyloxy, $C_3$-$C_6$-haloalkynyloxy, $C_1$-$C_6$-alkoxycarbonyl, $C_1$-$C_6$-alkenyloxycarbonyl, $C_1$-$C_6$-alkylamino, di($C_1$-$C_6$-alkyl)amino, tri($C_1$-$C_{10}$)alkylsilyl, or phenyl or a 5- to 7-membered saturated or partially unsaturated heterocyclic ring which contains 1 to 3 heteroatoms selected from the group consisting of oxygen, sulfur and nitrogen or a 5- to 6-membered heteroaromatic ring system which contains 1 to 4 heteroatoms selected from the group consisting of oxygen, nitrogen and sulfur, which phenyl and which heterocyclic or heteroaromatic ring may be bonded via an oxygen or a sulfur atom, wherein the above groups $R^3$ are unsubstituted, or the hydrogen atoms in these groups may all or in part be replaced with any combination of groups selected from $R^a$, or the moiety $R^3$-D-X—$R^1$ together may form a saturated or unsaturated ring of formula α

(α)

which may have 5 to 7 ring members and besides X, 1 to 2 further heteroatoms selected from the group consisting of oxygen, sulfur and nitrogen and which ring may be substituted with 1 to 5 groups selected from $R^a$, $R^a$ is each independently halogen, cyano, nitro, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, $C_3$-$C_8$-halocycloalkenyl, phenoxy, $OR^i$, $SR^i$, $S(=O)R^i$, $S(=O)_2R^i$, $NR^iR^j$, —$S(=O)_2NR^iR$, $C(=O)R^i$, $C(=O)OR^i$, $C(=O)NR^iR^j$, $C(=NOR^i)R^j$, —$NR^iC(=G)R^j$, —$N[C(=G)R^i]2$, —$NR^iC(=G)OR^j$, —$C(=G)NR^i$—$NR^j_2$, —$NR^iSO_2R^j$, $SiR^i_yR^j_{3-y}$ (y is 0 to 3), or phenyl or a 5- to 6-membered heteroaromatic ring which contains 1 to 4 heteroatoms selected from the group consisting of oxygen, nitrogen and sulfur, wherein the carbon atoms in phenyl or in the heteroaromatic ring may be substituted with 1 to 5 halogens;

with the proviso that if X is oxygen, then $R^3$ is selected from the group consisting of halogen, $C_1$-$C_{10}$-alkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl and tri($C_1$-$C_{10}$)alkylsilyl;

G is oxygen or sulfur;

$R^i$, $R^j$ are each independently hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_8$-halocycloalkyl, $C_3$-$C_6$-cycloalkenyl, or $C_3$-$C_6$-halocycloalkenyl; and Q is $C_1$-$C_{12}$-alkyl, $C_1$-$C_{12}$-haloalkyl, $C_2$-$C_7$-alkenyl, $C_2$-$C_7$-haloalkenyl, $C_2$-$C_7$-alkynyl, $C_2$-$C_7$-haloalkynyl, $C_3$-$C_7$-cycloalkyl, $C_3$-$C_7$-halocycloalkyl, $C_3$-$C_7$-cycloalkyl-$C_1$-$C_5$-alkyl, or $C_3$-$C_7$-halocycloalkyl-$C_1$-$C_5$-alkyl, wherein each group is unsubstituted or substituted with one or more, groups $C_3$-$C_7$-cycloalkyl, $C_3$-$C_7$-halocycloalkyl or tri($C_1$-$C_{10}$)alkylsilyl;

X is $S(=O)_n$, with the proviso that the following compounds are excluded:

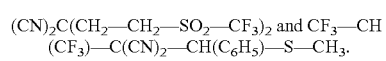

9. A method of protecting growing plants from attack or infestation by pests by applying to the plants, or to the soil or water in which they are growing, a pesticidally effective amount of a compound of claim 8.

10. A method for treating or protecting animals against infestation or infection by parasitical pests which comprises orally, topically or parenterally administering or applying to the animals a parasiticidally effective amount of a compound of formula (I) as defined in claim 8 or their or veterinarily acceptable salts.

11. A process for the preparation of a composition for treating or protecting animals against infestation or infection by parasitical pests which comprises mixing a parasiticidally effective amount of a compound of formula (I) as defined in claim 8 or a veterinarily acceptable salt thereof, with a veterinarity acceptable carrier.

12. A composition comprising a pesticidally active amount of a compound of claim 8 and an agronomically or veterinarily acceptable carrier.

13. A mixture comprising a compound of claim 8 and a pesticide selected from the organo(thio)phosphates, carbamates, pyrethroids, growth regulators, neonicotinoids, nicotinic receptor agonists/antagonists compounds, GABA antagonist compounds, macrocyclic lactone insecticides, METI I acaricides, METI II and III compounds, oxidative phosphorylation inhibitor compounds, moulting disruptor compounds, mixed function oxidase inhibitor compound, sodium channel blocker compounds, benclothiaz, bifenazate, cartap, flonicamid, pyridalyl, pymetrozine, sulfur, thiocyclam, N—R'-2,2-dihalo-1-R"cyclo-propanecarboxamide-2-(2,6-dichloro-ααα-tri-fluoro-p-tolyl)hydrazone or N—R'-2,2-di(R''')propionamide-2-(2,6-dichloro-ααα-trifluoro-p-tolyl)-hydrazone, wherein R' is methyl or ethyl, halo is chloro or bromo, R" is hydrogen or methyl and R'" is methyl or ethyl, and anthranilamide compounds of formula I'³
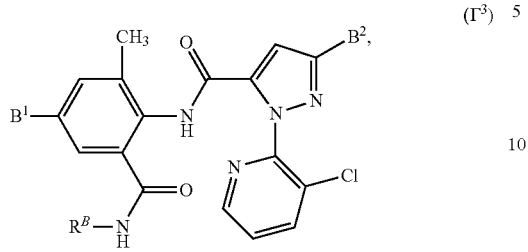
(I'³)
wherein $B^1$ is hydrogen, chlorine or cyano, $B^2$ is a bromine atom or $CF_3$, and $R^B$ is H, $CH_3$ or $CH(CH_3)_2$.
14. A veterinary medicament comprising a compound of claim 8 or a veterinarily acceptable salt thereof.
* * * * *